United States Patent
Burke et al.

(10) Patent No.: US 6,632,616 B2
(45) Date of Patent: Oct. 14, 2003

(54) COMPOUNDS THAT SELECTIVELY BIND TO EXPANDED POLYGLUTAMINE REPEAT DOMAINS AND METHODS OF USE THEREOF

(75) Inventors: James R. Burke, Chapel Hill, NC (US); Warren J. Strittmatter, Durham, NC (US); Yoshitaka Nagai, Osaka (JP)

(73) Assignee: Duke University, Durham, NC (US)

( * ) Notice: Subject to any disclaimer, the term of this patent is extended or adjusted under 35 U.S.C. 154(b) by 18 days.

(21) Appl. No.: 09/780,070

(22) Filed: Feb. 9, 2001

(65) Prior Publication Data

US 2002/0009752 A1 Jan. 24, 2002

Related U.S. Application Data

(60) Provisional application No. 60/189,781, filed on Mar. 16, 2000.

(51) Int. Cl.[7] .............................................. G01N 33/53
(52) U.S. Cl. ................................ 435/7.1; 435/6; 435/4; 530/350
(58) Field of Search .................... 435/7.1, 6, 4; 530/350

(56) References Cited

U.S. PATENT DOCUMENTS

| | | | |
|---|---|---|---|
| 5,504,190 A | | 4/1996 | Houghten et al. |
| 5,723,301 A | | 3/1998 | Burke et al. |
| 6,355,481 B1 | * | 3/2002 | Li et al. ...................... 435/311 |
| 6,420,122 B1 | * | 7/2002 | Housman et al. ............ 435/7.1 |

OTHER PUBLICATIONS

Wood et al, Molecular and Cellular Neuroscience, 11, 149–60(1998).*

Faber et al, Human Molecular Genetics, 7(9), 1463–1474 (1998).*

Nagai, Y., et al., *Identification of QBP1, a synthetic peptide that preferentially binds expanded polyglutamine domain by phage display technique*, Abstract (Oct. 1999).

Nagai, Yoshitaka, et al., *Inhibition of Polyglutamine Protein Aggregation and Cell Death by Novel Peptides Identified by Phase Display Screening*, The Journal of Biological Chemistry, vol. 275, No. 14, pp. 10437–10442 (2000).

Kola, Axel, et al., *Epitope mapping of a C5a neutralizing mAb using a combined approach of phage display, synthetic peptides and site–directed mutagenesis*, Immunotechnology, vol 2, pp. 115–126 (1996).

Imafuku, Ichiro, et al., *Polar Amino Acid–Rich Sequences Bind to Polyglutamine Tracts*, Biochemical and Biophysical Research Communications, vol. 253, pp. 16–20 (1998).

Schwarze, Steven R, et al., *In Vivo Protein Transduction: Delivery of a Biologically Active Protein into the Mouse*, Science, vol. 285, pp. 1569–72 (Sep. 3, 1999).

Onodera, Osamu, et al., *Oligomerization of Expanded Polyglutamine Domain Fluorescent Fusion Proteins in Cultured Mammalian Cells*, Biochemical and Biophysical Research Communications, vol. 238, pp. 599–605 (1997).

Moulder, Krista L., et al., *Generation of Neuronal Intranuclear Inclusions by Polyglutamine–GFP: Analysis of Inclusion Clearance and Toxicity as a Function of Polyglutamine Length*, The Journal of Neuroscience, vol. 19, No. 2, pp. 705–715 (Jan. 15, 1999).

Nagai, Yoshitaka, et al., *Expanded Polyglutamine Domain Proteins Bind Neurofilament and Alter the Neurofilament Network*, Experimental Neurology, vol. 155, pp. 195–203 (1999).

Supattapone, Surachai, et al., *Elimination of prions by branched polyamines and implications for therepeutics*, PNAS, vol. 96, No. 25, pp. 14529–14534 (Dec. 7, 1999).

Burke, James R., et al., *Huntingtina dn DRPLA proteins selectively interact with the enzyme GAPDH*, Nature Medicine, vol. 2, No 3, pp. 347–350 (Mar. 1996).

Onodera, Osamu, et al., *Toxicity of expanded polyglutamine–domain proteins in Escherichia coli*, Federation of European Biochemical Societies, vol. 399, pp. 135–139 (1996).

Schwarze, Steven R., et al., *In vivo protein transduction: intracellular delivery of biologically active proteins, compounds and DNA*, TiPS, vol. 21, pp. 45–48 (Feb. 2000).

Prochiantz, Alain, *Messenger proteins: homeoproteins, TAT and others*, Curr. Opin. Cell Biol., vol. 12, pp. 400–406 (2000).

Presentation Abstract, Nagai, Y., et al., *Identification of QBP1, a synthetic peptide that preferentially binds expanded polyglutamine domain by phase display technique*, http://www.faseb.org/genetics/ashg99/f2629.htm (Sep. 21, 1999).

* cited by examiner

Primary Examiner—T. D. Wessendorf
(74) Attorney, Agent, or Firm—Myers Bigel Sibley & Sajovec

(57) ABSTRACT

Compounds that selectively bind to expanded polyglutamine repeats are disclosed. Such compounds are characterized in that they bind to a first polyglutamine peptide consisting of 60 glutamine residues under conditions in which they do not bind to a second polyglutamine peptide consisting of 20 glutamine residues. Conjugates of such compounds, nucleic acids encoding the same, and methods of use thereof are also disclosed.

6 Claims, 8 Drawing Sheets

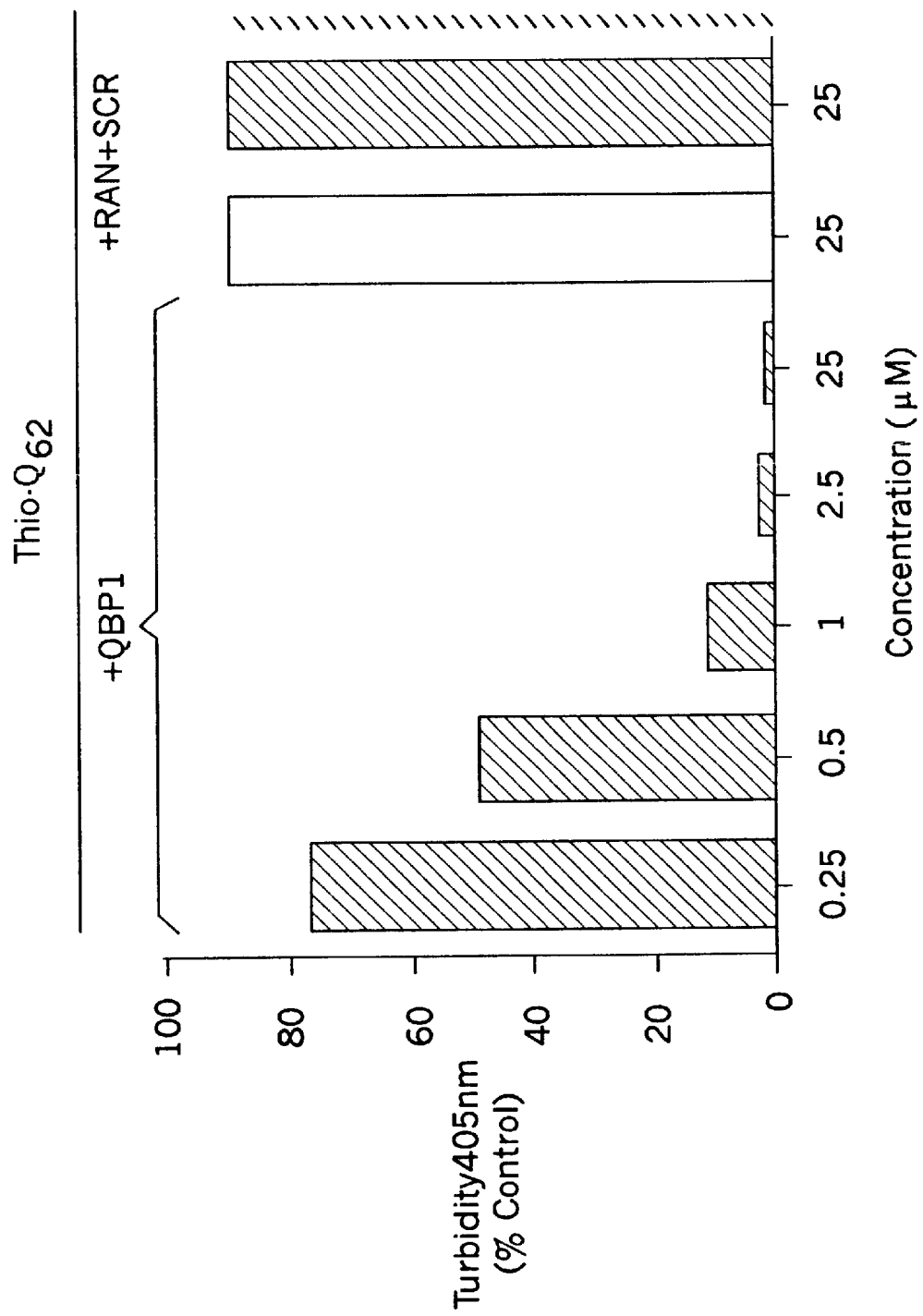

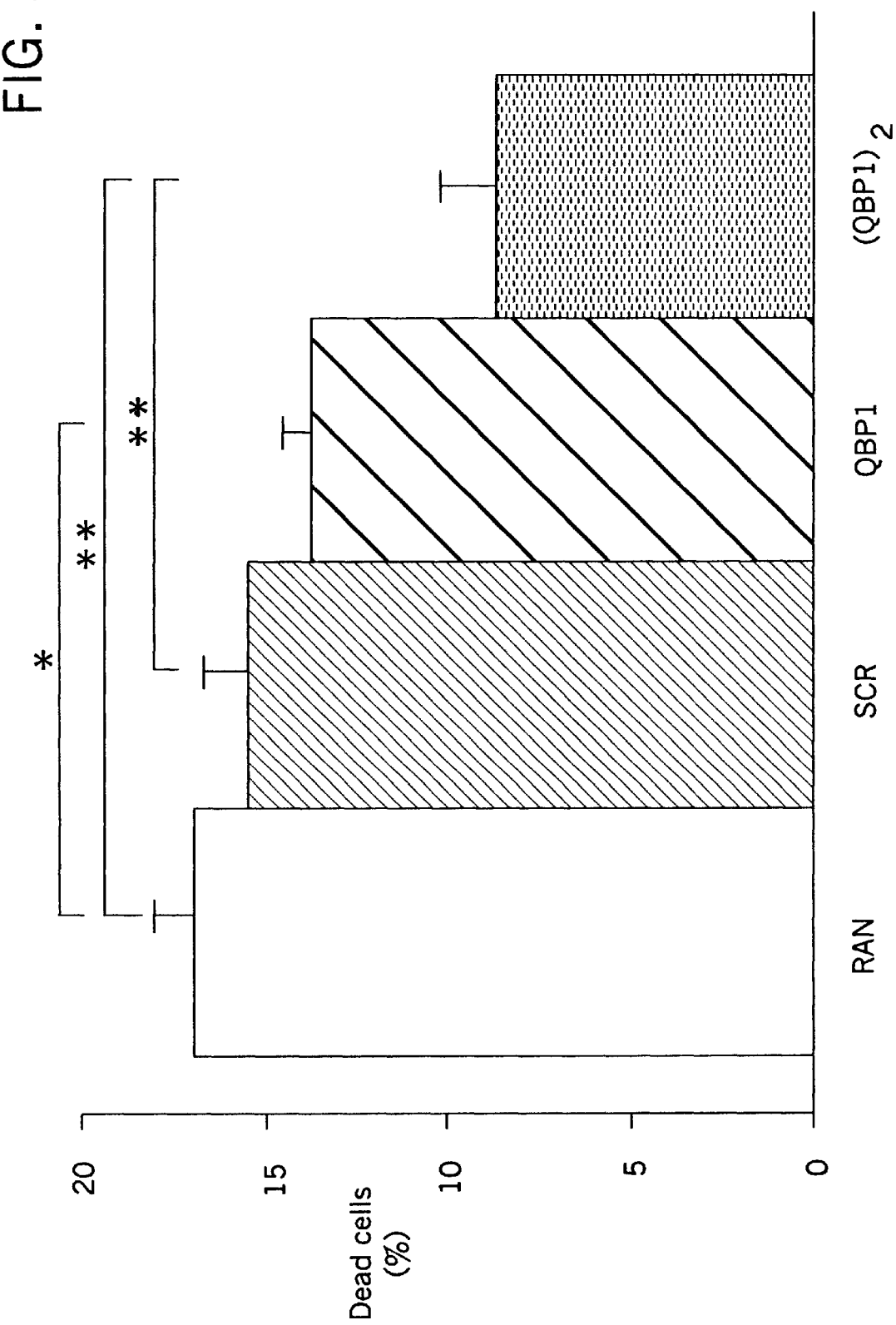

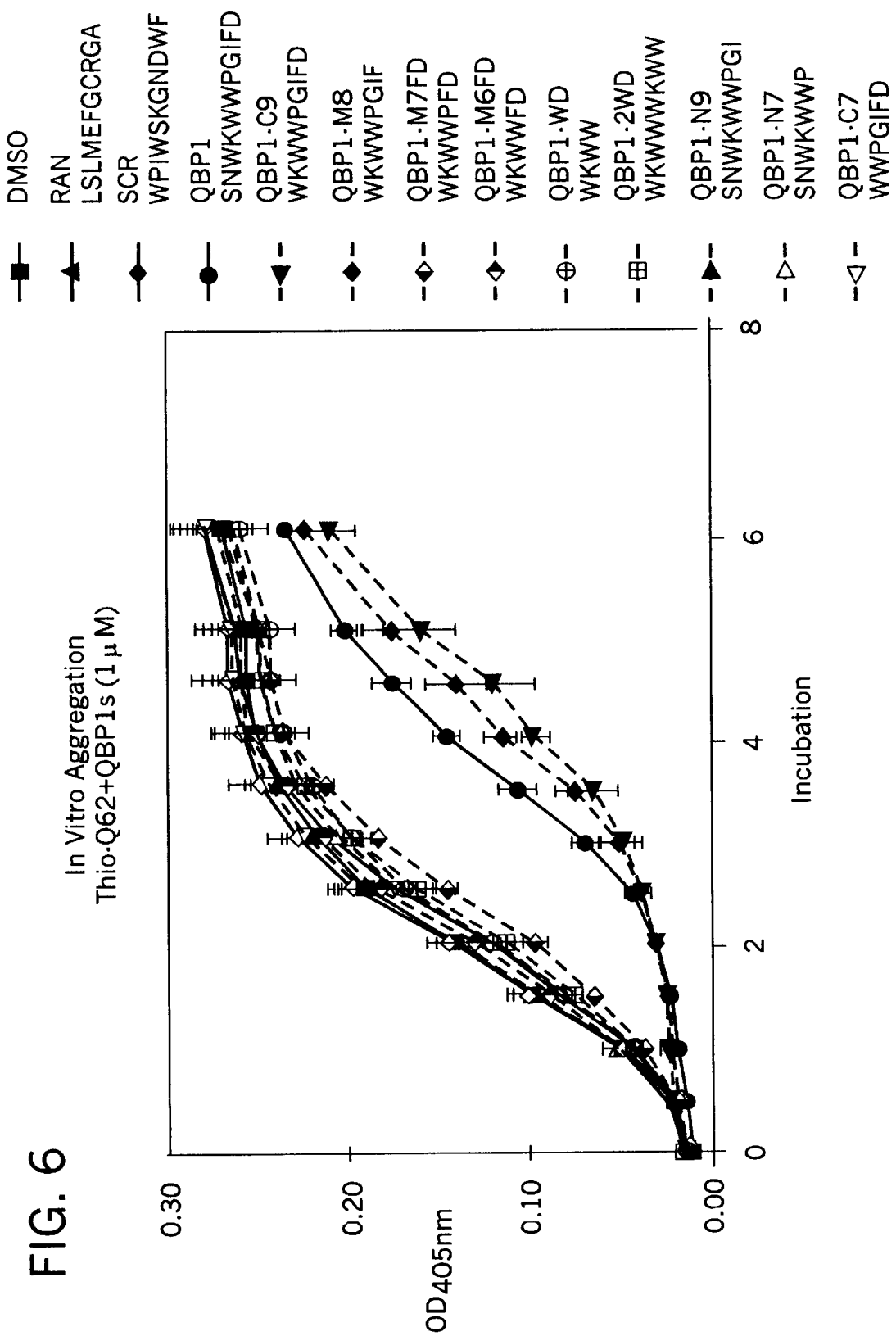

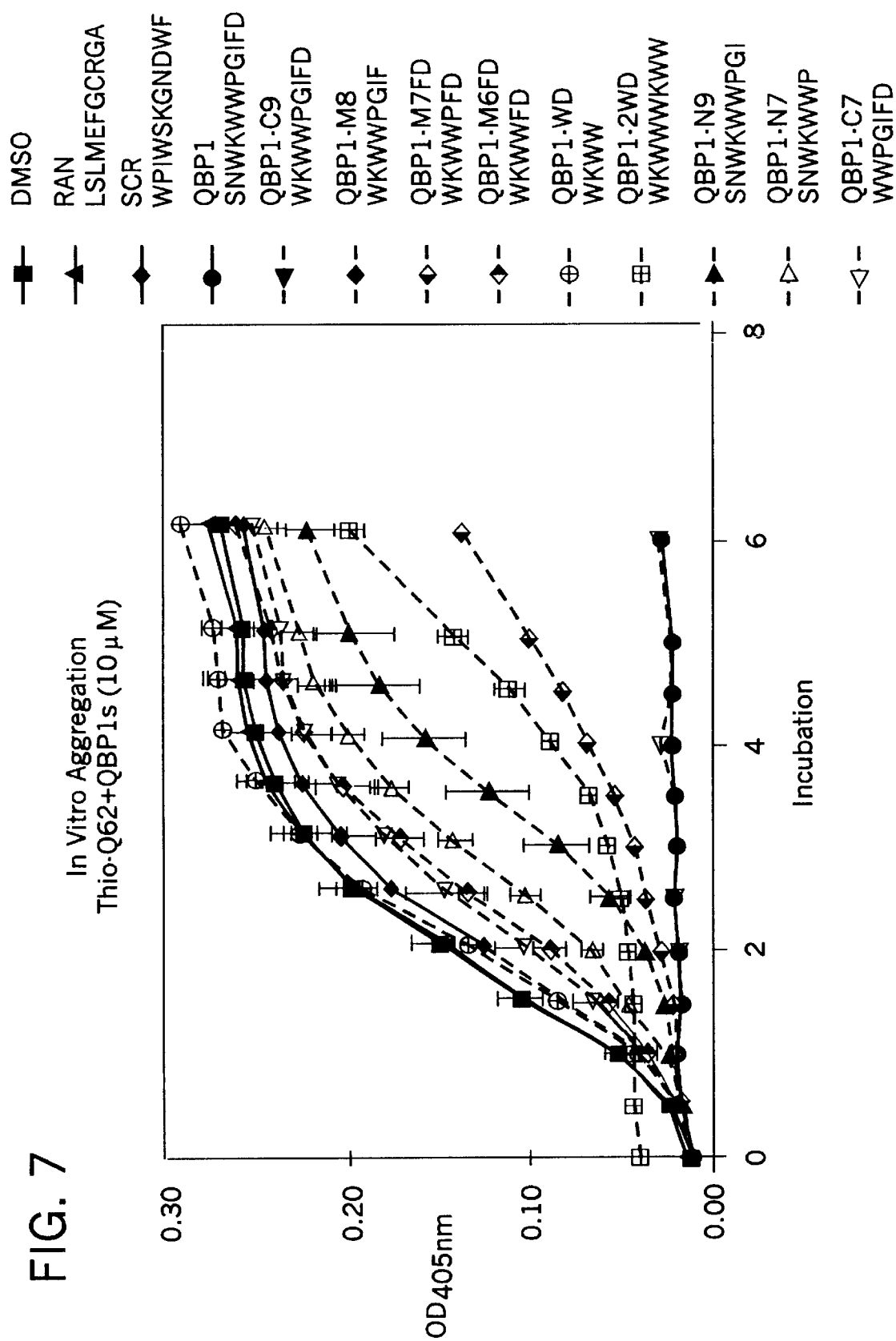

COMPOUNDS THAT SELECTIVELY BIND TO EXPANDED POLYGLUTAMINE REPEAT DOMAINS AND METHODS OF USE THEREOF

RELATED APPLICATIONS

This application claims the benefit of U.S. provisional application Ser. No. 60/189,781, filed Mar. 16, 2000, the disclosure of which is incorporated by reference herein in its entirety.

FIELD OF THE INVENTION

The present invention concerns compounds that selectively bind to expanded CAG repeat regions in DNA which encode expanded polyglutamine regions in certain disease proteins, methods of treatment employing such compounds, and assay procedures employing such compounds.

BACKGROUND OF THE INVENTION

Eight inherited neurodegenerative diseases, including Huntington's disease (HD), dentatorubral pallidoluysian atrophy (DRPLA), spinobulbar muscular atrophy and spinocerebellar ataxia types 1, 2, 3, 6 and 7, are caused by expanded CAG repeats in the coding region of the disease genes (Koshy, B. T. and Zoghbi, H. Y., *Brain Pathol* 7, 927–942 (1997); Paulson, H. L. and Fischbeck, K. H, *Ann Rev Neurosci*, 19, 79–107 (1996); Paulson, H. L., *Am J Hum Genet* 64, 339–3450 (1999)). The CAG codon is translated into glutamine (Q), and the polyglutamine domain is the only region of homology among the eight disease proteins. The length of the repeat is the critical determinant of age-of-disease onset, with repeat length greater than 40 glutamines producing neurodegeneration in seven of the eight diseases.

Proteins with pathologic-length polyglutamine domains display novel properties that are not present in these proteins when they contain a shorter polyglutamine domain. Length-dependent polyglutamine-protein interactions are reported for Huntington-associated protein 1 (HAP-1), GAPDH, leucine-rich acidic nuclear protein, vimentin, neurofilament, apopain, calmodulin, WW domain proteins and Ras-related nuclear protein/ARA24 (Li, X. J. et al., *Nature* 378, 398–402 (1995); Burke, J. R. et al, *Nature Med* 2, 347–350 (1996); Matilla, A. et al. *Nature* 389, 974–978 (1997); Onodera, 0. et al., *Biochem & Biophys Res Commun* 238, 599–605. (1997); Nagai, Y. et al. m *Exp Neurol* 155, 195–203 (1999); Goldberg, Y. P. et al., *Nature Genet* 13, 442–449 (1996); Bao, J. et al., *Proc Natl Acad Sci USA* 93, 5037–5042 (1996); Faber, P. W. et al., *Hum Mol Genet* 7, 1463–1474. (1998); Hsiao, P. W. et al., *J Biol Chem* 274, 20229–20234 (1999)).

Proteins with expanded polyglutamine domains also aggregate and aggregation is a pathologic hallmark of the polyglutamine repeat diseases (Hackam, A. S. et al. *J Cell Biol* 141, 1097–1105 (1998); Perez, M. K. et al. *J Cell Biol* 143, 1457–1470 (1998)). These polyglutamine length-dependent properties may arise from the ability of long polyglutamine domains to adopt unique three-dimensional conformations and serve to confer the disease proteins with a pathologic gain-of-function (Perutz, M. F. *Trends Biochem Sci* 24, 58–63 (1999); Lansbury, P. T. J. *Proc Natl Acad Sci USA* 96, 3342–3344 (1999)).

Lansbury proposed that during the initial stages of folding of expanded-polyglutamine proteins, misfolded intermediates interact with themselves (homologous interactions) or other proteins (heterologous interactions) leading to critical cell injury (supra). Supporting this hypothesis of length-dependent alteration in tertiary structure, Trottier et al. identified a monoclonal antibody (mAb1C2) that preferentially recognizes proteins with long, but not short, polyglutamine domains (Trottier, Y. et al., *Nature* 378, 403–406 (1995)). Shorter peptides that selectively bind pathologic-length polyglutamine regions would be useful in inhibiting interaction with other proteins, thereby slowing, or preventing, disease pathology, and in rational drug design. However, such peptides have not previously been developed.

SUMMARY OF THE INVENTION

Accordingly, the present invention provides compounds that selectively bind to expanded polyglutamine repeats. For example, such a compound is characterized in that it binds to a first polyglutamine peptide consisting of 60 glutamine residues under conditions in which the compound does not bind to a second polyglutamine peptide consisting of 20 glutamine residues. The compound are represented by Formula I:

$$X^1-R^{11}R^{12}R^{13}R^{14}-Y^1 \qquad (1)$$

wherein:

$R^{11}$ is Trp;

$R^{12}$ is (i) Trp or (ii) a charged amino acid such as Lys, Arg or His (preferably Lys or Arg, and most preferably Lys);

$R^{13}$ is (i) Trp or (ii) a charged amino acid such as Lys, Arg or His (preferably Lys or Arg, and most preferably Lys);

subject to the proviso that one of $R^{12}$ and $R^{13}$ is Trp and the other is a charged amino acid;

$R^{14}$ is Trp;

$X^1$ is a polypeptide consisting of from zero to 5, 10 or 20 or 30 amino acids, preferably standard amino acids; and $Y^1$ is a polypeptide consisting of from zero to 5, 10 or 20 or 30 amino acids, preferably standard amino acids;

or a physiologically or pharmaceutically acceptable salt thereof. Compositions comprising compounds as described above in a pharmaceutically acceptable carrier, and the use of such compounds for the preparation of a medicament for the treatment of disorders as described herein, are also aspects of the present invention.

Compounds of the invention may be conjugated to a detectable group (e.g., a fluorescent group, an enzyme), a heterologous protein or peptide, etc. in accordance with known techniques. Detectable groups may or may not be a heterologous protein or peptide. The heterologous protein or peptide may be a translocation peptide (or "transduction peptide").

A second aspect of invention is a nucleic acid (e.g., a DNA, an RNA) encoding a compound as described above (including those conjugated to a heterologous protein or peptide), along with constructs comprising such nucleic acids operatively associated with a promoter, transfer vectors (e.g., plasmids, viruses, etc.) containing such constructs, and cells that contain and express such nucleic acids and constructs.

A third aspect of the present invention is a method of treating a cell that contains and expresses a protein having an expanded polyglutamine region, the method comprising administering to the cell a treatment effective amount of a compound as described above. The administering step may be carried out directly, e.g., by administering the compound per se (including as a pharmaceutically acceptable salt) directly to the cell, or indirectly by administering a vector that encodes and expresses the compound in the cell (with the nucleic acid that encodes and expresses that compound acting as an intermediate). The compound may be administered as a conjugate with a heterologous protein or peptide, particularly a translocation peptide, as described above.

A fourth aspect of the invention is a method of treating a subject afflicted with a nneurodegenerative disease characterized by the presence of expanded polyglutamine repeats. The method comprises administering to the subject a treatment effective amount of a compound as described above. Again, the administering step may be carried out directly, by administering the compound per se, or indirectly by administering a vector that encodes and expresses the compound in cells of the subject being treated. Again, the compound may be administered as a conjugate with a heterologous protein or peptide, particularly a translocation peptide, as described above.

A further aspect of the invention is the use of compounds or vectors as described above for the preparation of a medicament for carrying out a method as described above.

A fifth aspect of the invention is a method of detecting an expanded polyglutamine domain in a sample suspected of containing the same. The method comprises the steps of: (a) contacting a sample suspected of containing an expanded polyglutamine domain to a compound as described above, and then (b) detecting the presence or absence of binding of the compound to the sample, the presence of binding indicating the presence of an expanded polyglutamine domain in the sample. typically, the method is carried out by conjugating the compound to a detectable group, and then determining the presence or absence of binding of the detectable group to the sample. For example, the compound may be conjugated to thioredoxin, and the detecting step may be carried out by turbidometric assay.

A sixth aspect of the present invention is a method of screening compounds (e.g., in a high throughput screening procedure) for activity in treating an expanded polyglutamine repeat disease. The method comprises the steps of (a) providing a reagent system comprising an expanded polyglutamine segment conjugated to thioredoxin; (b) combining the test compound with the reagent system; and then (c) determining the presence or absence of aggregation in the reagent system (e.g., by turbidometric assay) the absence of aggregation indicating that the compound is a candidate for activity in treating an expanded polyglutamine repeat disease.

A seventh aspect of the present invention is a method of screening compounds (e.g., in a high throughput screening procedure) for activity in treating an expanded polyglutamine repeat disease. The method comprises the steps of (a) providing a reagent system comprising: (i) a first compound comprising an expanded polyglutamine segment conjugated to a first signal group and (ii) a second compound comprising an expanded polyglutamine segment conjugated to a second signal group, wherein the first and second fluorescent groups when conjugated together generate a detectable event (e.g., the emission of a signal, the quenching of a signal), and wherein each of the expanded polyglutamine segments consists of at least 40 polyglutamine residues; then (b) combining the test compound with the reagent system; and then (c) determining the presence or absence of the detectable signal,; the absence of the detectable signal indicating that the compound is a candidate for activity in treating an expanded polyglutamine repeat disease. A preferred embodiment includes: (i) a first compound comprising an expanded polyglutamine segment conjugated to a first fluorescent group and (ii) a second compound comprising an expanded polyglutamine segment conjugated to a second fluorescent group, wherein the first and second fluorescent groups are members of a fluorescence resonance energy transfer (FRET) pair, and wherein each of the expanded polyglutamine segments consists of at least 40 polyglutamine residues; then (b) combining the test compound with the reagent system; and then (c) determining the presence or absence of fluorescence resonance energy transfer between the first and second fluorescent groups; the absence of fluorescence resonance energy transfer indicating that the compound is a candidate for activity in treating an expanded polyglutamine repeat disease.

The present invention is explained in greater detail in the drawings herein and the specification set forth below.

BRIEF DESCRIPTION OF THE DRAWINGS

FIG. 2. Polyglutamine binding peptide inhibition of thioredoxin-$Q_{62}$ aggregation. QBP 1 inhibits thio-$Q_{62}$ aggregation in a concentration-dependent pattern (Filled bars). A random peptide (RAN; Open bar) and a scrambled version of QBP1 (SCR; Hatched bar), at 25 μM, inhibited thio-$Q_{62}$ aggregation less than 10%. Aggregation was assayed by turbidity at 405 nm (Hackam, A. S. et al. (1998) *J Cell Biol* 141, 1097–1105). Results shown are from representative experiments (n=4). Variation between duplicate wells was less than 10%.

FIG. 3. Intracellular distribution of $Q_n$-YFP and QBP1-CFP in COS 7 cells.

Figure 1A:
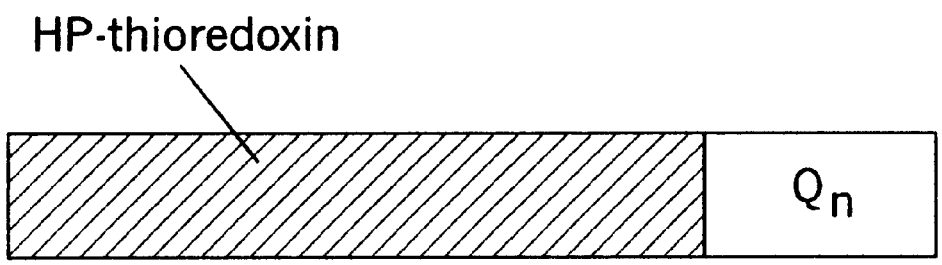
FIG. 1A. Schematic representation of thioredoxin-polyglutamine fusion protein. HP-Thioredoxin=His-Patch thioredoxin. $Q_n$=polyglutamine domain containing n sequential glutamines.

COS-7 cells examined 48 hours after transfection using a Zeiss fluorescence microscope with the CFP/YFP filter set from Omega Optical Inc. The percentage of cells with aggregates was calculated by counting the number of transfected cells containing aggregate and dividing by the total number of transfected cells multiplied times 100. In each experiment at least 200 transfected cells were counted. Experiments were repeated at least four times. Error bars represent standard errors. *=p<0.05;**=p<0.01 (Student's t-test)

FIG. 5. QBP1 expression inhibits polyglutamine-mediated cell death. Open bar=cells co-transfected with $Q_{57}$-YFP and RAN-CFP. Hatched bar=cells co-transfected with $Q_{57}$-YFP and SCR-CFP. Filled bar=cells co-transfected with $Q_{57}$-YFP and QBP1-CFP. Dotted bar=cells co-transfected with $Q_{57}$-YFP and (QBPI)$_2$-CFP. COS-7 cells examined 48 hours after transfection using a Zeiss fluorescence microscope with rhodamine filter set. The percentage of dead cells was calculated by counting the number of transfected cells stained with ethidium homodimer and dividing by the total number of transfected cells multiplied times 100. In each experiment at least 200 transfected cells were counted. Experiments were repeated at least three times. Error bars represent standard errors. *=p<0.05; **=p<0.01 (Student's t-test).

FIG. 6. In vitro aggregation of thio-Q62 plus QBP1s at 1 microMolar.

FIG. 7. In vitro aggregation of thio-Q62 plus QBP1s at ten microMolar.

DETAILED DESCRIPTION OF THE PREFERRED EMBODIMENTS

Proteins that contain polyglutamine repeats which may, or may not, be expanded, include, but are not limited to, huntingtin, atrophin 1, ataxin 1, ataxin 2, ataxin 6, ataxin 7, androgen receptor, etc.

Neurodegenerative diseases characterized by an expanded polyglutamin repeat (sometimes also referred to as expanded polyglutamine repeat diseases), and with which the present invention is concerned, include but are not limited to Huntington's disease, dentatorubral pallidoluysian atrophy, spinobulbar muscular atrophy, and spinocerebellar ataxia types 1, 2, 3, 6 and 7.

The term "expanded polyglutamine domain" or "expanded polyglutamine segment", as used herein, refers to a polyglutamine segment or domain that consists of at least 40 consecutive glutamine residues linked by peptide bonds. Such an expanded polyglutamine segment may exist per se as an isolated polypeptide, or may exist within a protein that contains a polyglutamine repeat that may or may not be expanded, as described above. Such expanded segments are found in subjects afflicted with a polyglutamine repeat disease, whether or not the subject has shown manifest symptoms.

Subjects to be treated by the methods of the present invention, or upon which diagnostic or prognostic methods as described herein are carried out, are typically human subjects, but may also be animal subjects (particularly mammalian subjects) such as dogs, cats, rats, mice, insects, etc., for veterinary purposes, or for drug design and screening purposes. The subjects may be afflicted with a polyglutamine repeat disease, or at risk of developing symptoms associated with a polyglutamine repeat disease, a subject suspected of being afflicted with a polyglutamine repeat disease, or a subject being screened for a polyglutamine repeat disease.

As used herein, the terms "combating", "treating" and "ameliorating" are not necessarily meant to indicate a reversal or cessation of the disease process underlying the condition afflicting the subject being treated. Such terms indicate that the deleterious signs and/or symptoms associated with the condition being treated are lessened or reduced, or the rate of progression is reduced, compared to that which would occur in the absence of treatment. A delay in onset of symptoms is a desirable treatment object, as is a reduction in frequency of symptom episodes (e.g., for seizures). A change in a disease sign or symptom may be assessed at the level of the subject (e.g., the function or condition of the subject is assessed), or at a tissue or cellular level. Where the methods of the present invention are used to treat chronic CNS conditions (such as Huntington's disease), the methods may slow or delay the onset of symptoms such as dementia, while not necessarily affecting or reversing the underlying disease process.

A "Symptom" which may be treated by the methods of the present invention may be any one, or combination of, chorea, dementia, ataxia, seizures, and psychiatric symptoms such as psychosis or depression.

As used herein, "combinatorial library" refers to collections of diverse oligomeric molecules of differing sequence, which can be screened simultaneously for activity as a ligand for a particular target, such as an expanded polyglutamine repeat domain. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

"Aggregation" as used herein refers to mutiple molecular interactions between polyglutamine repeat containing proteins, and/or other proteins, resulting in a loss of solubility (including a partial decrease in solubility).

"Translocation peptide" or "transduction peptide" refers to a peptide or protein (or active fragment or domain thereof) that moves a protein from one cell compartment to another, and particularly from the extracellular space through the cell or plasma membrane into the cell. Examples include the TAT transduction domain (see, e.g., S. Schwarze et al., *Science* 285 (Sep. 3, 1999); penetratins or penetratin peptides (D. Derossi et al., *Trends in Cell Biol.* 8, 84–87); and Herpes simplex virus type 1 VP22 (A. Phelan et al., *Nature Biotech.* 16, 440–443 (1998). Translocation peptides are conjugated or coupled to a compound of Formula I, to, among other things, produce a conjugate compound that may easily pass into target cells, or through the blood brain barrier and into target cells.

1. Peptides and Peptide Analogs

All peptide sequences mentioned herein are written according to the usual convention whereby the N-terminal amino acid is on the left and the C-terminal amino acid is on the right. A short line (or no line) between two amino acid residues indicates a peptide bond.

The symbols $X^1$, $Y^1$, Z, $R^{10}$, $R^{11}$, and the like; and Ser, Leu or the like, as found in a peptide sequence herein stands for an amino acid residue, i.e., =N—CH(R)—CO—when it is at the N-terminus, or —NH—CH(R)—CON= when it is at C-terminus, or —NH—CH(R)—CO— when it is not at the N— or C-terminus, where R denotes the side chain (or identifying group) of an amino acid or its residue, or a group of amino acid residues linked by peptide bonds (or other pseudopeptide bonds as described below). For example, R is —CH2 COOH for Asp, R is —H for Gly, R is —CH$_2$ OH for Ser, R is —CH3 for Ala and R is —$CH_2CH_2CH_2CH_2NH_2$ for Lys. Also, when the amino acid residue is optically active, it is the L-form configuration that is intended unless the D-form is expressly designated.

In describing peptides of this invention, the conventional and non-conventional abbreviations for the various amino acids are used. They are listed for clarity below:

Standard amino acids with nonpolar R groups:
Ala=A=Alanine
Val=V=Valine
Leu=L=Leucine
Ile=I=Isoleucine
Pro=P=Proline
Phe=F=Phenylalanine
Trp=W=Tryptophan
Met=M=Methionine
Standard amino acids with uncharged polar R groups:
Gly=G=Glycine
Ser=S=Serine
Thr=T=Threonine
Cys=C=Cysteine
Tyr=Y=Tyrosine
Asn=N=Asparagine
Gln=Q=Glutamine
Acidic standard amino acids (negatively charged at pH 6.0)
Asp=D=Aspartic Acid
Glu=E=Glutamic Acid
Basic standard amino acids (positively charged at pH 6.0)
Lys=K=Lysine
Arg=R=Arginine
His=H=Histidine
Some nonstandard amino acids:
Orn=Ornithine
Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=.alpha.-aminonormalbutyric acid
Dip=2,2-diphenylalanine
Thz=4-Thiazolylalanine As noted above, the present invention provides compounds of Formula I:

$$X^1—R^{11}R^{12}R^{13}R^{14}—Y^1 \quad (I)$$

wherein:
$R^{11}$ is Trp;
$R^{12}$ is (i) Trp or (ii) a charged amino acid such as Lys, Arg or His (preferably Lys or Arg, and most preferably Lys);
$R^{13}$ is (i) Trp or (ii) a charged amino acid such as Lys, Arg or His (preferably Lys or Arg, and most preferably Lys);
subject to the proviso that one of $R^{12}$ and $R^{13}$ is Trp and the other is a charged amino acid;

$R^{14}$ is Trp;
$X^1$ is a polypeptide of from zero to 5, 10, 20 or 30 amino acids or more, preferably standard amino acids (where zero indicates the polypeptide is deleted or absent); and
$Y^1$ is a polypeptide of from zero to 5, 10, 20 or 30 amino acids or more; preferably standard amino acids.
$X^1$ may, for example, be $R^1R^2R^3R^4R^5$, wherein:
$R^1$ is any amino acid, or is deleted;
$R^2$ is any amino acid, or is deleted;
$R^3$ is any amino acid, or is deleted;
$R^4$ is any amino acid, or is deleted; and
$R^5$ is any amino acid, or is deleted.
$Y^1$ may, for example, be $R^{20}R^{21}R^{22}R^{23}R^{24}$, wherein:
$R^{20}$ is any amino acid, or is deleted;
$R^{21}$ is any amino acid, or is deleted;
$R^{22}$ is any amino acid, or is deleted;
$R^{23}$ is any amino acid, or is deleted; and
$R^{24}$ is any amino acid, or is deleted.

Compounds of Formula I above are preferably polypeptides consisting of from 4 or 5 amino acid residues to 40, 50, 60, or 80 amino acid residues.

One preferred group of compounds of Formula I above are compounds of Formula Ia:

$$X^1—R^{11}R^{12}R^{13}R^{14}R^{15}—Y^2 \quad (Ia)$$

wherein:
$R^{11}$, $R^{12}$, $R^{13}$, $R^{14}$, and $X^1$ are as given above;
$R^{15}$ is Pro, Gly, Cys, Ser or Met, preferably Pro, Gly, Cys or Ser, and most preferably Pro; and
$Y^2$ is a polypeptide of from zero to 5, 10, 20 or 29 amino acids, preferably standard amino acids.

Another preferred group of compounds of Formula I above are compounds of Formula Ib:

$$X^2—R^{10}R^{11}R^{12}R^{13}R^{14}—Y^1 \quad (Ib)$$

wherein:
$R^{11}$, $R^{12}$, $R^{13}$, $R^{14}$, and $Y^1$ are as given above;
$R^{10}$ is Pro, Gly, Cys, Ser or Met, preferably Pro, Gly, Cys or Ser, and most preferably Pro; and
$X^2$ is a polypeptide of from zero to 5, 10, 20 or 29 amino acids, preferably standard amino acids.

Another preferred group of compounds of Formula I above are compounds of Formula Ic:

$$X^1—R^{11}R^{12}R^{13}R^{14}R^{15}R^{16}R^{17}R^{18}—Y^3 \quad (Ic)$$

wherein:
$R^{11}$, $R^{12}$, $R^{13}$, $R^{14}$, $R^{15}$ and $X^1$ are as given above;
$R^{16}$ is Gly, Pro or Cys, preferably Gly or Pro, and most preferably Gly;
$R^{17}$ is Ile, Ala, Val or Leu, preferably Ila, Val or Leu, and most preferably Ile (or is deleted);
$R^{18}$ is Phe, His, Tyr or Trp, preferably Phe, His or Tyr, and most preferably Phe (or is deleted); and
$Y^3$ is a polypeptide of from zero to 5, 10, 20 or 26 amino acids, preferably standard amino acids.

Another preferred group of compounds of Formula I above are compounds of Formula Id:

$$X^3—R^7R^8R^9R^{10}R^{11}R^{12}R^{13}R^{14}—Y^1 \quad (Id)$$

wherein:
$R^{10}$, $R^{11}$, $R^{12}$, $R^{13}$, $R^{14}$, and $Y^1$ are as given above;
$R^9$ is Gly, Pro or Cys, preferably Gly or Pro, and most preferably Gly;

$R^8$ is Ile, Ala, Val or Leu, preferably Ila, Val or Leu, and most preferably Ile (or is deleted);

$R^7$ is Phe, His, Tyr or Trp, preferably Phe, His or Tyr, and most preferably Phe (or is deleted); and $X^3$ is a polypeptide of from zero to 5, 10, 20 or 26 amino acids, preferably standard amino acids.

Specific examples of compounds according to Formula I above include, but are not limited to:

WKWW (SEQ ID NO:1);
WWKW (SEQ ID NO:2);
SNWKWWPGIFD (QBP1) (SEQ ID NO:3);
SNWKWWPGIFDSNWKWWPGIFD (SEQ ID NO:4);
WKWWWKWW (SEQ ID NO:5);
WKWWP (SEQ ID NO:6)
PWWKW (SEQ ID NO:7);
WKWWPG (SEQ ID NO:8);
GPWWKW (SEQ ID NO:9);
WKWWPGI (SEQ ID NO:10);
IGPWWKW (SEQ ID NO:11);
WKWWPGIF (SEQ ID NO:12);
FIGPWWKW (SEQ ID NO:13);
WKWWPFD (SEQ ID NO:14);
DFPWWKW (SEQ ID NO: 15);
WKWWPWKWW (SEQ ID NO:16);
WWKWPWWKW (SEQ ID NO:17);
WKWWFD (SEQ ID NO:18); and
FDWWKW (SEQ ID NO:19).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. Non-limiting examples of some substitutions that can be made are as follows:

Ala may be replaced with Val or Ser;
Val may be replaced with Ala, Leu, Met, or Ile, preferably Ala or Leu;
Leu may be replaced with Ala, Val or Ile, preferably Val or Ile;
Gly may be replaced with Pro or Cys, preferably Pro;
Ile may be replaced with Ala, Val or Leu, preferably Leu or Val;
Pro may be replaced with Gly, Cys, Ser, or Met, preferably Gly, Cys, or Ser;
Cys may be replaced with Gly, Pro, Ser, or Met, preferably Pro or Met;
Met may be replaced with Pro or Cys, preferably Cys;
His may be replaced with Phe or Gln, preferably Phe;
Phe may be replaced with His, Tyr, or Trp, preferably His or Tyr;
Tyr may be replaced with His, Phe or Trp, preferably Phe or Trp;
Trp may be replaced with Phe or Tyr, preferably Tyr;
Asn may be replaced with Gln or Ser, preferably Gln;
Gln may be replaced with His, Lys, Glu, Asn, or Ser, preferably Asn or Ser;
Ser may be replaced with Gln, Thr, Pro, Cys or Ala;
Thr may be replaced with Gln or Ser, preferably Ser;
Lys may be replaced with Gln or Arg;
Arg may be replaced with Lys, Asp or Glu, preferably Lys or Asp;
Asp may be replaced with Lys, Arg, or Glu, preferably Arg or Glu; and
Glu may be replaced with Arg or Asp, preferably Asp.

Once made, changes can be routinely screened to determine their effects on the function of the corresponding peptide by screening procedures described herein.

Peptides of the present invention may be made in accordance with techniques known in the art. Using accepted techniques of chemical synthesis, the peptide may be built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

In another aspect, the invention may be carried out with dimeric analogs of the compounds of the present invention. The dimer may be formed by either including two of the same peptides of Formula I, or two different peptides of Formula I. In one embodiment, the dimer is formed by utilizing a dicarboxylic acid linker capable of binding to a free amine, either primary or secondary, located within each peptide. See, e.g., R. Vavrek and J. Stewart, Peptides: Structure and Function 381–384 (Pierce Chemical Co. 1983). Examples of suitable dicarboxylic acid linkers are succinic acid, glutamic acid, and phthalic acid. In other embodiments, the dimer is formed by utilizing an amino acid linker capable of binding to a free amine group of one peptide and a free carboxyl group of the other peptide.

In yet another aspect, the invention features compounds of Formula I having at least one pseudopeptide bond between amino acid residues. By "pseudopeptide bond" is meant that the carbon atom participating in the bond between two residues is reduced from a carbonyl carbon to a methylene carbon, i.e., $CH_2$ —NH; or less preferably that of CO—NH is replaced with any of $CH_2$ —S, $CH_2$ —$CH_2$, $CH_2$ —O, or $CH_2$ —CO. In addition, such pseudopeptide bond analogs can be used to form dimeric analogs as is described above. A detailed discussion of the chemistry of pseudopeptide bonds is given in Coy et al., *Tetrahedron* 44:835–841 (1988).

Compounds of Formula I may be conjugated to a heterologous protein or peptide, such as a translocation peptide, in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science* 247, 28029 (1990); Rossmann, *Nature* 333, 392 (1988); Weis et al., *Nature* 333, 426 (1988); James et al., *Science* 260, 1937 (1993) (development of benzodiazepine peptidomimetic compounds based on the structure and function of tetrapeptide ligands).

Non-peptide mimetics of the peptides of the present invention are also an aspect of this invention. Non-protein drug design may be carried out using computer graphic modeling to design non-peptide, organic molecules able to bind to the expanded polyglutamine region. See, e.g., Knight, *BIO/Technology* 8, 105 (1990); Itzstein et al, *Nature* 363, 418 (1993) (peptidomimetic inhibitors of influenza virus enzyme, sialidase). Itzstein et al., *Nature* 363, 418 (1993), modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al., *Science* 263, 380 (1994) regarding the rational design of bioavailable nonpeptide cyclic ureas that function as HIV protease inhibitors. Lam et al. used information from x-ray crystal structure studies of HIV protease inhibitor complexes to design nonpeptide inhibitors.

2. Physiological Pharmaceutical Salts

The active compounds disclosed herein can, as noted above, be prepared and administered in the form of their pharmaceutically acceptable salts. Pharmaceutically acceptable salts are salts that retain the desired biological activity of the parent compound and do not impart excessive toxicological effects to the subject; physiologically acceptable salts are likewise salts that retain the desired biological activity and do not impart excessive toxicological effects to the cell to which the compound is administered. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

3. Nucleic Acids, Constructs and Vectors

As noted above, the present invention provides nucleic acids (e.g., a DNA, an RNA) encoding a compound as described above, along with constructs comprising such nucleic acids operatively associated with a promoter, transfer vectors (e.g., plasmids, viruses, etc.) containing such constructs, and cells (e.g., mammalian cells, particularly human cells) that contain and express such nucleic acids and constructs. The production of such constructs is well known in the art, along with methods of transforming cells to contain such constructs. An alternative group of active compounds that may be administered to cells or subjects as described herein, in an appropriate carrier (e.g., a pharmaceutical formulation as described below), include typical gene therapy vectors. Suitable vectors are typically viral vectors, including DNA viruses, RNA viruses, and retroviruses. Techniques for utilizing vector deliver systems and carrying out gene therapy are known in the art. Herpesvirus vectors, adenovirus vectors, adeno-associated virus (or AAV) vectors are particular types of vectors that may be employed in administering compounds of the present invention through incorporation of a nucleic acid that encodes the compound of Formula I and expresses that compound in a host cell.

4. Pharmaceutical Formulations

The active compounds described above (including the pharmaceutically acceptable salts thereof) may be formulated for administration in a pharmaceutical carrier in accordance with known techniques. See, e.g., Remington, *The Science And Practice of Pharmacy* ($9^{th}$ Ed. 1995).

In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, nasal, inhalation (e.g., to the lungs), buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for oral administration may be controlled release or osmotic dosage forms, as described in U.S. Pat. Nos. 5,576,022 and 5,698,244.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for nasal, parenteral, or inhalation administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

Further, the present invention provides liposomal formulations of the active compounds disclosed herein. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the compounds disclosed herein, may be lyophilized to produce a lyophilizate which may be reconstituted with a pharmaceutically acceptable carrier, such as water, to regenerate a liposomal suspension.

Other pharmaceutical compositions may be prepared from the compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

5. Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, nasal, inhalation (e.g., to the lungs) parenteral, intramuscular, intradermal, or intravenous, and transdermal administration.

The therapeutically effective dosage or treatment effective amount of any one active agent, the use of which is in the scope of present invention, will vary somewhat from compound to compound, and patient to patient (depending upon the age and condition of the subject), and will depend upon factors such as the age and condition of the patient and the route of delivery. Such dosages can be determined in accordance with routine pharmacological procedures known to those skilled in the art.

In general, the daily dose in the case of oral administration is typically in the range of 0.01 or 0.1 to 100 or 500 mg/kg body weight, and the daily dose in the case of parenteral (e.g., subcutaneous) administration is typically in the range of 0.0001 or 0.001 to 50 or 100 mg/kg body weight. Daily dosages may be administered in a single unit or multiple units each day.

Administration may be carried out on a chronic or acute basis. When the administering step is an acute administering step, the active agent may (for example) be given as a single dosage as above, or daily in the above dosages for a period of 2 days 5 days. Where the administering step is a chronic administrating step, the daily dosage will be given at least 3, 4 or 5 times a week (e.g., seven days a week) for a period of at least two weeks, at least a month, at least two months, or even at least six months or more. When a chronic dosage regimen is completed the patient may be reevaluated and the administration continued or modified as necessary.

As used herein, the term "administering to the brain of a subject" refers to the use of routes of administration, as are known in the art, that provide the therapeutic compound to the central nervous system tissues, and in particular the brain, of a subject being treated.

The blood-brain barrier presents a barrier to the passive diffusion of substances from the bloodstream into various regions of the CNS. However, active transport of certain agents is known to occur in either direction across the blood-brain barrier. Substances that may have limited access to the brain from the bloodstream can be injected directly into the cerebrospinal fluid. Cerebral ischemia and inflammation are also known to modify the blood-brain barrier and result in increased access to substances in the bloodstream.

Administration of a therapeutic compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present therapeutic compounds.

Pharmacologic-based procedures are also known in the art for circumventing the blood brain barrier, including the conversion of hydrophilic compounds into lipid-soluble drugs. The active agent may be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with therapeutic compounds to be delivered to the interstitial fluid compartment of the brain, to cause an increase in the permeability of the blood-brain barrier and effect increased delivery of the therapeutic compounds to the brain. Intravenous or intraperitoneal administration may also be used to administer the compounds of the present invention.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives. The carrier may be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

An alternative method of administering peptides of the present invention is carried out by administering to the subject a vector carrying a nucleic acid sequence encoding the peptide, where the vector is capable of entering brain cells so that the peptide is expressed and secreted, and is thus available to microglial cells. Suitable vectors are typically viral vectors, including DNA viruses, RNA viruses, and retroviruses. Techniques for utilizing vector deliver systems and carrying out gene therapy are known in the art. Herpesvirus vectors are a particular type of vector that may be employed in administering compounds of the present invention.

6. Assay Procedures

As discussed above, the present invention provides methods of detecting an expanded polyglutamine domain in a sample (e.g., a patient sample) suspected of containing the same. Such methods typically comprise the steps of: (a) contacting a sample suspected of containing an expanded polyglutamine domain to a compound as described above, and then (b) detecting the presence or absence of binding of the compound to the sample, the presence of binding indicating the presence of an expanded polyglutamine domain in the sample. Typically, the method is carried out by conjugating the compound to a detectable group (e.g., an enzyme, a fluorescent group), and then determining the presence or absence of binding of the detectable group to the sample. For example, the compound with a detectable group could be hybridized to a patient's or subject's protein blot (which protein blot can be produced on a substrate in accordance with known techniques). The compound would bind only if a protein with an expanded polyglutamine repeat were present. The sample for the blot may comprise a protein, which may be collected from a patient or subject and purified as necessary in accordance with standard techniques.

7. High Throughput Screening Procedures

A limiting factor to identifying new therapeutic agents for expanded polyglutamine repeat diseases is the lack of a high throughput screening assay. Aggregation of polyglutamine proteins in vitro has been previously described, but these assays either require proteolytic cleavage of polyglutamine fusion proteins or employ detection systems (such as dynamic light scattering) not readily adaptable for rapid screening (Scherzinger, E. et al (1999) *Proc Natl Acad Sci U S A* 96, 4604–4609; Saudou, F. et al. (1998) *Cell* 95, 55–66). This application provides a simple, in vitro assay of polyglutamine aggregation that facilitates the identification of compounds that inhibit aggregation. Aggregation of thioredoxin-polyglutamine conjugate (thio-$Q_n$) protein in vitro faithfully recapitulates the behavior of polyglutamine proteins in human disease. As shown here, thio-$Q_n$ aggregation occurs in vitro only with repeats longer than 35; in HD, the most common polyglutamine repeat disease, individuals develop disease only if they express a huntingtin protein with more than 36 sequential glutamines (Rubinsztein, D. C. et al. (1996) *Amer J Human Genet* 59, 16–22). In vitro, thio-$Q_n$ protein with longer pathologic-length polyglutamine domains aggregates more rapidly and at lower concentration than with shorter pathologic-length glutamine domains; similarly, in HD polyglutamine domain length directly correlates with earlier age of onset, severity of clinical phenotype and aggregate formation (Martindale, D. et al (1998) *Nature Genetics* 18, 150–154). The ability to identify compounds that selectively alter intracellular interactions and metabolism of pathologic-length polyglutamine domain proteins may be an effective therapeutic strategy in these diseases.

In general, such an assay comprises the steps of (a) providing a reagent system comprising an expanded polyglutamine segment conjugated to thioredoxin; (b) combining the test compound with the reagent system; and then (c) determining the presence or absence of aggregation in the reagent system (e.g., by turbidometric assay) the absence of aggregation indicating that the compound is a candidate for activity in treating an expanded polyglutamine repeat disease.

An alternative embodiment of the foregoing is an assay employing fluorescence resonance energy transfer. Such a method comprises the steps of (a) providing a reagent system comprising: (i) a first compound comprising an expanded polyglutamine segment conjugated to a first fluorescent group and (ii) a second compound comprising an expanded polyglutamine segment conjugated to a second fluorescent group, wherein the first and second fluorescent groups are members of a fluorescence resonance energy transfer (FRET) pair, and wherein each of the expanded polyglutamine segments consists of at least 40 polyglutamine residues; then (b) combining the test compound with the reagent system; and then (c) determining the presence or absence of fluorescence resonance energy transfer between the first and second fluorescent groups; the absence of fluorescence resonance energy transfer indicating that the compound is a candidate for activity in treating an expanded polyglutamine repeat disease. Other signal groups that, when conjugated together generate a detectable event (e.g., the emission of a signal or the quenching of a signal) may also be employed.

In a preferred embodiment of the foregoing, either the first or second test compound (e.g., containing either the donor or acceptor member of the FRET pair) is immobilized on a solid support, so that the absence of fluorescence at the solid support can be measured.

In the foregoing screening assays, the test compound may be a member of a combinatorial library. In either system, the reagent system may be an in vitro (cell free) system, and the combining step is carried out by adding the test compound to the in vitro system. Alternatively, in either assay, the reagent system may be an in vivo cell system, and the combining step may be carried out by adding the test compound to the in vivo cell system (e.g., by expressing the test compound in the cell, or by introducing the test compound into the cell).

The present invention can be used with test compounds, or libraries (where groups of different test compounds are employed), of any type. In general, such test compounds are organic compounds, including but not limited to that may be used to carry out the present include oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide, herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. If desired, numerous methods of synthesizing or applying such test compounds on solid supports (where the test compound may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

First and second fluorescent compounds, or fluoropohores, that can be used to carry out the present invention can be selected based on the physical properties thereof, as is known in the art of fluorescence resonance energy transfer (FRET), the two being selected so that they together comprise the donor and acceptor fluorophores of an FRET pair. Either the first or the second fluorophore can serve as the donor fluorophore, with the other serving as the acceptor fluorophore.

FRET is a distance-dependent interaction between the electronic excited states of two fluorophores in which excitation is transferred from a donor molecule to an acceptor molecule without emission of a photon. In general, the primary conditions for FRET are (i) that the donor and acceptor molecules be in close proximity to one another (typically 1 or 10 to 100 or 200 Angstroms); (ii) that the absorption spectrum of the acceptor overlap the fluorescence emission spectrum of the donor; and (iii) that the donor and acceptor transition dipole orientations be approximately or essentially parallel. Examples of suitable donor and acceptor pairs include:

cyan fluorescent protein and yellow fluorescent protein;
fluorescein and tetramethylrhodamine;
5-(2'-aminoethyl) aminonaphthalene-1-sulfonic acid (EDANS) and fluorescein;
EDANS and 4-(4'-dimethylaminopheylazo)benzoic acid (DABCYL);
fluorescein and fluorescein; and
4,4-difluoro-5-(2-thienyl)-4-bora-3a,4a diaza-5-indacene-3-propionic acid (BODIPY FL) and BODIPY FL.

See generally R. Haugland, Handbook of Fluorescent Probes and Research Chemicals (Sixth Ed. 1995). Abbreviations that are standard in the art are used herein. Note also that the present invention can be carried out when the donor and acceptor fluorophores are the same, with FRET being detected by the resulting fluorescence emission. *Biophys. J.* 69, 1565 (1995). One or both of the fluorophores can be a fluorescent protein such as green fluorescent protein, and it is particularly advantageous to employ a fluorescent protein as the fluorophore when the test compound is a protein or peptide by preparing a fusion protein of the test compound and a fluorescent protein.

The present invention is explained in greater detail in the following non-limiting Examples. The abbreviations used herein are: HD, Huntington's disease; DRPLA, dentatorubral pallidoluysian atrophy; HAP-1, Huntingtin-associated protein 1; GAPDH, glyceraldehyde-3-phosphate dehydrogenase, $Q_n$, polyglutamine domain with n sequential glutamines; mAb1C2, monoclonal antibody directed against expanded polyglutamine repeats; $Q_n$-GST, polyglutamine-glutathione-S-transferase fusion protein with n sequential glutamines; thio-$Q_n$, thioredoxin-polyglutamine fusion protein with n sequential glutamines; QBP1, glutamine binding peptide 1; $(QBP1)_2$, tandem repeat of QBP1; SCR, scrambled QBP1; RAN, random peptide, CFP, cyan fluorescent protein, YFP, yellow fluorescent protein.

EXAMPLES 1–13

Inhibition of Polyglutamine Protein Aggregation and Cell Death by Novel Peptides Identified by Phage Display Screening In these examples, several polyglutamine-binding peptides are identified and the ability of one of these peptides to inhibit polyglutamine aggregation is demonstrated both in a novel in vitro assay and in cultured cells. These examples further demonstrate that expression of a tandem repeat of a polyglutamine-binding peptide in cell culture inhibits polyglutamine-induced cell death.

EXAMPLE 1

Phage Display Screening

Phage display library construction and screening were performed as described (Adey, N. B. et al. (1996) in *Phage Display of Peptides and Proteins* (Kay, B. K., Winter, J., and McCafferty, J., eds) pp. 66–78, Academic Press, San Diego; Sparks, A. B. et al., (1996) in *Phage Display of Peptides and Proteins* (Kay, B. K., Winter, J., and McCafferty, J., eds) pp. 227–254, Academic Press, San Diego). Briefly, 33-mer nucleotides were ligated to the 5' terminus of the pIII gene of phage M13 to generate a peptide library with 11 amino acids added to the amino terminus of the pIII protein. Individual phage libraries were screened for binding to a polyglutamine-glutathione-S-transferase fusion protein with 62 glutamines ($Q_{62}$-GST). Construction of the polyglutamine-GST vectors was previously described (Onodera, O. et al. (1996) *FEBS Letters* 399, 135–139). $Q_{62}$-GST was immobilized on 96 well plates at a concentration of 2.5 µg/ml in 100 mM $NaHCO_3$ pH 8.5. The wells were then blocked with 0.1% BSA to decrease nonspecific binding. After blocking, the plates were washed with PBS-0.1% Tween-20 and phage incubated for 7 hours at room temperature. Unbound phage were removed by extensive washing with PBS containing 0.1% Tween-20. Bound phage were eluted sequentially with 50 mM glycine pH 2.0 and 100 mM ethanolamine prewarmed to 50° C. Selected phage were isolated and DNA sequenced. ELISA assays were performed to quantify bound phage using horseradish peroxidase anti-phage antibody (Pharmacia).

EXAMPLE 2

Thioredoxin-polyglutamine Constructs and Protein Purification

The CAG repeat of polyglutamine-GST vectors was amplified by PCR and ligated into the NcoI and EcoRI site of the pThio-His B vector (Invitrogen, San Diego, Calif.) (Onodera, O. et al. (1996) *FEBS Letters* 399, 135–139). The sequence of the clones and the length of the CAG repeats were confirmed by DNA sequencing. Thioredoxin-polyglutamine fusion protein was produced in transformed *E. coli* DH5α and purified using BPER lysis buffer (Pierce Chemical Comp., Rockford, Ill.) and Pro-Bond columns (Invitrogen, San Diego, Calif.) according to manufacturer's instructions. Purified thioredoxin-polyglutamine fusion protein was dialyzed against PBS pH 7.4 and concentration determined by Modified Lowry reaction (Pierce).

EXAMPLE 3

Thioredoxin-polyglutamine Protein Turbidity Assay

Turbidity assays were performed in 200 µl reactions consisting of thioredoxin-polyglutamine in PBS in 96-well, low protein binding plates. Plates were incubated at 4° C. and turbidity measured at 405 nm on a Thermo Max plate reader (Molecular Devices).

EXAMPLE 4

Peptide Synthesis

Peptides were synthesized at the Howard Hughes Medical Institute peptide sequencing facility at Duke University with an acetylated amino terminus and protection of tryptophan with BOC during synthesis. Identical results were obtained with peptides obtained from Bio-Synthesis Inc. (Lewisville, Tex.). Stock solutions of peptides were prepared fresh daily by dissolving in dimethyl sulfoxide at 2.5 mM and incubated with thioredoxin-polyglutamine protein at 0.25–25 µM.

EXAMPLE 5

Constructs for Protein Expression in Cell Culture

The CAG repeat of the $Q_n$-GFP vector (Onodera, O. et al. (1996) *FEBS Letters* 399, 135–139) were inserted into the XhoI and EcoRI sites of the pEYFP-N1 vector (Clontech, Palo Alto, Calif.) to construct the $Q_n$-YFP vectors. The polyglutamine-binding peptide and control constructs were prepared by ligating synthetic oligonucleotides into the XhoI and BamHI sites of the pECFP-N1 vector (Clontech) to obtain glutamine binding peptide 1-CFP (QBP1-CFP), scrambled QBP1-CFP (SCR-CFP), and a computer-generated random peptide-CFP (RAN)-CFP. The insert of QBP1-CFP was duplicated by PCR to obtain a tandem repeat of QBP1-CFP (($QBP1)_2$-CFP). The sequence of all constructs was confirmed by DNA sequencing. The first methionine of YFP or CFP was changed to isoleucine by PCR site-directed mutagenesis to eliminate translation of the fluorescent protein without the polyglutamine domain. The sizes of the fluorescent fusion proteins were confirmed by western blotting.

EXAMPLE 6

Cell Culture and Fluorescence Microscopy

COS-7 cells were grown and maintained in Dulbecco's modified Eagles' medium (DMEM) supplemented with 10% fetal calf serum (FCS). Cells were transfected with Effectene according to manufacturer's instructions (Qiagen GmbH, Hilden, Germany). Cells were examined 48 hours after transfection using a Zeiss fluorescence microscope equipped with YFP/CFP filter sets (Omega Optical Inc., Brattleboro, Vt.). The percentage of cells with aggregates was calculated by dividing the number of cells with aggregates by the total number of fluorescent cells, multiplied by 100. Cell viability was examined 48 hours after transfection using ehtidium homodimer (Molecular Probes, Eugene, Oreg.). Cells were incubated with 5 µM ethidium homodimer for 30 minutes (37° C.) and then examined under a fluorescence microscope equipped with a rhodamine filter set. Cells with nuclear fluorescence were counted as dead. In each experiment at least 200 transfected cells were counted. Cells expressing random peptide-CFP (RAN-CFP) and polyglutamine-YFP ($Q_n$-YFP) were used as a control to calculate the relative difference in aggregate formation and cell death. Experiments were repeated at least four times.

EXAMPLE 7

Identification of Peptides that Preferentially Bind Protein With a Pathologic Length Polyglutamine Domain A peptide phage display library was screened to identify peptides that interact with proteins containing a pathologic-length polyglutamine domain. The M13 phage display library was constructed to contain a random 11 amino acid peptide inserted at the amino terminus of the Piii capsid protein (Onodera, O. et al. (1996) *FEBS Letters* 399, 135–139). The 11-mer peptide was not completely random since a fixed amino acid was inserted in the sixth position of the peptide ($X_5$—fixed—$X_5$) to decrease the vast number of possible peptides ($20^{11}$) and permit more thorough sampling. $2.5 \times 10^{11}$ phage from each of the following fixed amino acid libraries were screened for binding to a polyglutamine-glutathione-S-transferase fusion protein with 62 glutamines ($Q_{62}$-GST): aspartate, phenylalanine, histidine, lysine, leucine, proline, and tryptophan (Sparks, A. B. et al., (1996) in *Phage Display of Peptides and Proteins* (Kay, B. K., Winter, J., and McCafferty, J., eds) pp. 227–254, Academic Press, San Diego; Isacson, O. et al.(1995) *Nature Medicine* 1, 1189–1194). After four rounds of successive screening, 350 polyglutamine-binding phage clones were isolated. The selected phage were then assayed by ELISA for binding to normal-($Q_{19}$) or pathologic-length ($Q_{62}$) polyglutamine-GST. Six phage clones bound $Q_{62}$-GST greater than $Q_{19}$-GST (Binding ratios of $Q_{62}$-GST to $Q_{19}$-GST: 1.23–1.66) and had their DNA sequenced to elucidate peptide sequence (Table 1; Glutamine (Q) Binding Peptides 1 through 6: QBP1–6).

TABLE 1

Phage display peptides with preferential binding to $Q_{62}$-GST.[1]

| SEQUENCE (5 x 5) | RATIO Q62/Q19 BINDING ELISA | NAME |
| --- | --- | --- |
| SNWKW*W*PGIFD (SEQ ID NO:3) | 1.66 | QBP1 |
| HWWRS*W*YSDSV (SEQ ID NO:20) | 1.31 | QBP2 |
| HEWHW*W*HQEAA (SEQ ID NO:21) | 1.30 | QBP3 |
| WGLEH*F*AGNKR (SEQ ID NO:22) | 1.27 | QBP4 |
| WWRWN*W*ATPVD (SEQ ID NO:23) | 1.25 | QBP5 |
| WHNYF*H*WWQDT (SEQ ID NO:24) | 1.23 | QBP6 |
| WPIWSKGNDWF (SEQ ID NO:25) | Scrambled QBP1 | SCR |
| LSLMEFGCRGA (SEQ ID NO:26) | Random 11-mer | RAN |
| SNWKW*W*PGIFDSNWKW*W*PGIFD (SEQ ID NO:4) | Tandem QBP1 | (QBP1)$_2$ |

[1]The 11 amino acid inserts in the Piii protein were designed with 5 random amino acids, one fixed amino acid (shown here underlined), and 5 random amino acids in a $X_5$-fixed-$X_5$ format. Each purified phage was assayed for binding to immobilized $Q_{62}$- and $Q_{19}$-GST by ELISA. Bound phage was detected with monoclonal antibody against M13 phage (Pharmacia). Binding ratios were determined by amount of phage bound to $Q_{62}$ divided by phage bound to $Q_{19}$. None of these clones bound bovine serum albumin (used as a blocking agent during incubation) or GST alone

EXAMPLE 8

In vitro Aggregation of Thioredoxin-polyglutamine

We then developed an in vitro aggregation assay to examine whether these polyglutamine-binding peptides inhibit polyglutamine aggregation. Polyglutamine-GST proteins are not ideal for studying polyglutamine aggregation since the polyglutamine domain does not aggregate unless it is cleaved from the GST moiety (Scherzinger, E. et al. (1997) *Cell* 90, 549–558; Scherzinger, E. et al (1999) *Proc Natl Acad Sci U S A* 96, 4604–4609). To circumvent this limitation, we produced thioredoxin-polyglutamine fusion proteins (thio-$Q_n$; where n=the number of consecutive glutamine residues. Thioredoxin is highly soluble, can be expressed at high concentrations in *Escherichia coli* and is easily purified (Yasukawa, T. et al. (1995) *J Biol Chem* 270, 25328–25331). The length of the expressed glutamine domains was chosen to survey a range of normal and pathologic repeat lengths (Normal: 19 and 35 glutamines; Pathologic: 62 and 81 glutamines) (FIG. 1A).

To monitor thioredoxin-polyglutamine protein aggregation a turbidometric assay was developed, similar to the assays commonly used to study microtubule assembly and β-amyloid aggregation (Jarrett, J. T. et al. (1993) *Biochem* 32, 4693–4697; Sloboda, R. D. et al. (1976) *Biochem* 15, 4497–4505). Solutions of thio-$Q_{62 \; and \; 81}$ protein increased turbidity in a polyglutamine length-, time- and concentration-dependent manner (FIG. 1B and C; Time dependence of aggregation of thioredoxin-polyglutamine with 81 glutamines not shown). To demonstrate that turbidity was produced by aggregated thioredoxin-polyglutamine protein containing 62 or 81 glutamines (thio-$Q_{62 \; or \; 81}$), the insoluble material was pelleted by centrifugation or captured on a 0.22 μm filter. The pelleted and retained material was confirmed as thioredoxin-polyglutamine fusion protein containing 62 or 81 glutamines on western blots probed with anti-thioredoxin or anti-polyglutamine antibody (not shown). In contrast, thioredoxin-polyglutamine protein containing 19 or 35 glutamines (thio-$Q_{19 \; or \; 35}$) was not pelleted by centrifugation and was not trapped by a 0.22 μm filter.

Figure 1B:
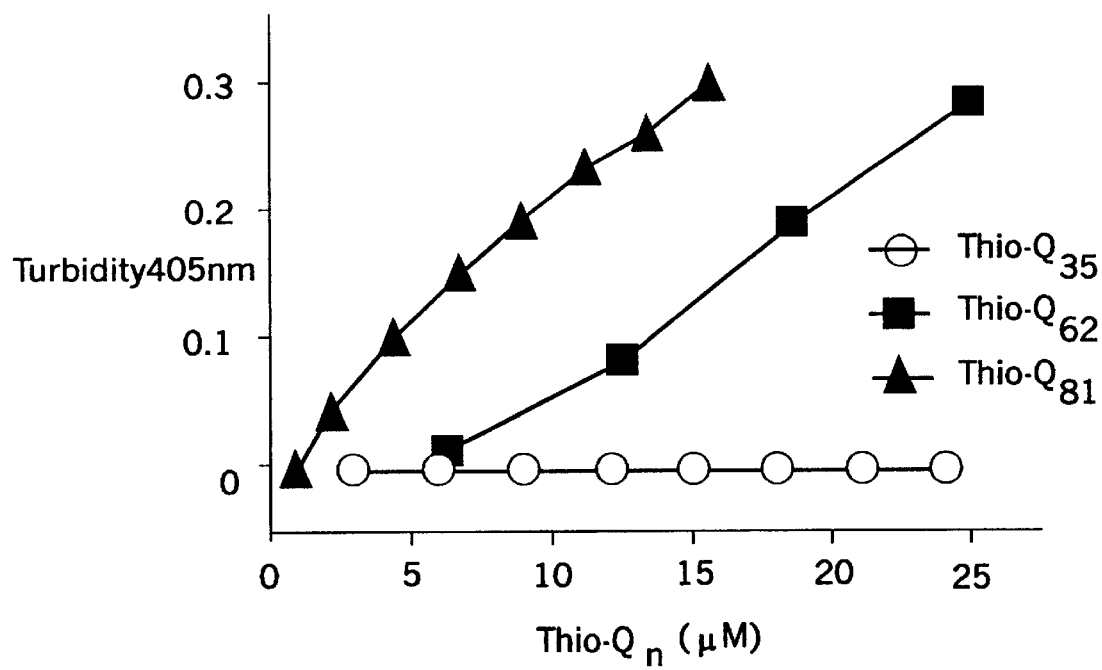
FIG. 1B. Concentration curve of thioredoxin-$Q_n$ protein aggregation. Thio-$Q_n$ proteins containing pathologic-length glutamine repeats aggregate in vitro. Thio-$Q_{81}$ (□) aggregates at lower concentration than thio-$Q_{62}$ (□), while thio-$Q_{35}$ (□) does not aggregate.
Figure 1C:
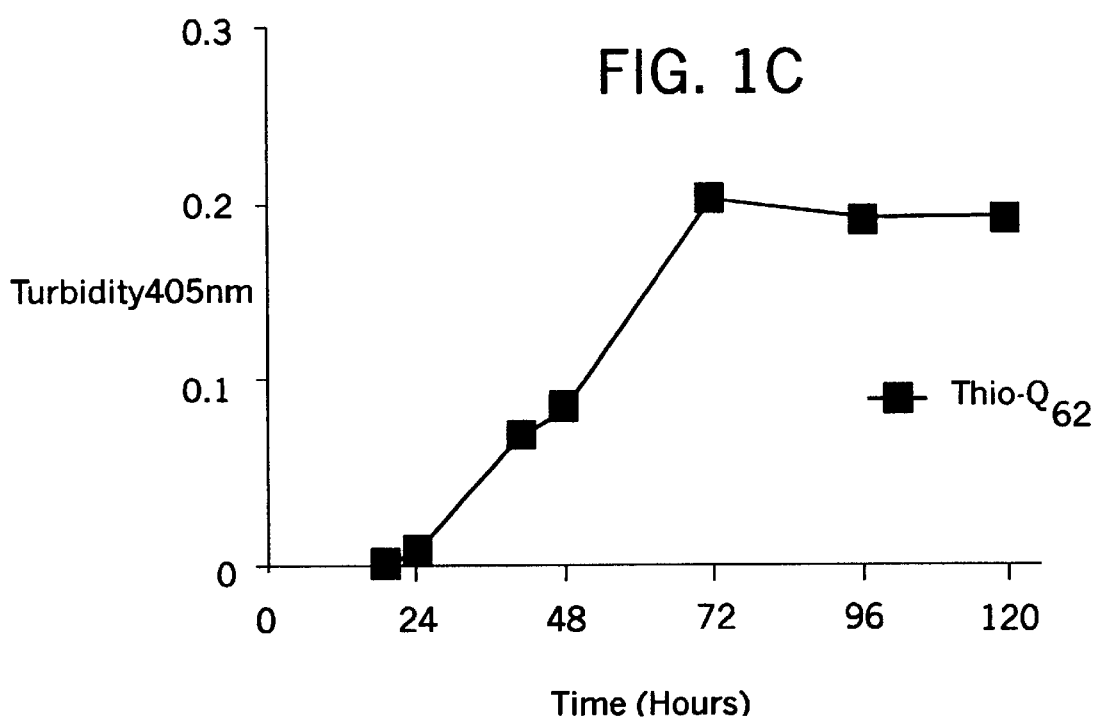
FIG. 1C. Time-course of thioredoxin-$Q_{62}$ protein aggregation. Thio-$Q_{62}$ (□) aggregation consists of a lag phase followed by rapid polymerization. Thio-$Q_{62}$ concentration 17 μM. In FIGS. B and C, plateau is reached by 72 hours incubation. Turbidity measured at 405 nm following a 72 hour incubation (13). Results shown are from representative experiments (n=4). Variation between duplicate wells was less than 10%.

In this turbidity assay, thioredoxin-polyglutamine protein containing 81 glutamines (thio-$Q_{81}$) aggregated faster (not shown) and at lower concentrations than thioredoxin-polyglutamine containing 62 glutamines (thio-$Q_{62}$)(FIG. 1B). Aggregation did not occur in solutions of thioredoxin-polyglutamine containing 62 glutamines at concentrations lower than 5 μM. As shown in FIG. 1C, macroscopic aggregation started following a lag period, consistent with a reaction with two kinetic components, an initial slow phase (similar to nidus formation in crystal growth) and a second rapid polymerization phase (Scherzinger, E. et al (1999) *Proc Natl Acad Sci U S A* 96, 4604–4609). Turbidity of thioredoxin-polyglutamine fusion protein containing non-pathologic glutamine repeats (19 or 35 glutamines) at concentrations ranging up to 50 μM did not change after 3 weeks at 4° C.

EXAMPLE 9

QBP1 Inhibits Thioredoxin-polyglutamine Aggregation

Next, the effect of these combinatorially-generated polyglutamine binding peptides on polyglutamine aggregation in vitro was examined. The 11-mer peptide was synthesized with the greatest differential binding to pathologic-length compared to normal length polyglutamine ($Q_{62}$/$Q_{19}$) (QBP1, Table 1). This peptide was chosen because it displayed the greatest selective binding to expanded polyglutamine domain proteins and, therefore, might preferentially block pathologic protein interactions.

The 11-mer peptide QBP1 potently inhibited aggregation of thioredoxin-polyglutamine protein with 62 glutamines (thio-$Q_{62}$) in vitro (FIG. 2). QBP1 completely inhibited thio-$Q_{62}$ aggregation at a molar ratio of 3:1 (thio-$Q_{62}$: QBP1) (FIG. 2). QBP1 was less potent at inhibiting aggregation of thioredoxin-polyglutamine protein with 81 glutamines (thio-$Q_{81}$) and required a 10-fold molar excess (1:10 thio-$Q_{81}$: QBP1) for complete inhibition (not shown). A scrambled sequence peptide of QBP1 (SCR; Table 1); and a computer-generated random 11 amino acid peptide (RAN; Table 1) did not inhibit aggregation (FIG. 2). Addition of QBP1 after aggregation did not reverse aggregation of thioredoxin-polyglutamine protein with 62 glutamines (thio-$Q_{62}$)(not shown). QBP1, scrambled (SCR) and random (RAN) peptides had no effect on the turbidity of the non-pathologic thioredoxin-polyglutamine proteins with 19 or 35 glutamines (thio-$Q_{19 \; or \; 35}$, Thio-$Q_{19}$ not shown).

EXAMPLE 10

QBP1 Co-localizes With Polyglutamine Aggregate in Cells

Next, it was determined whether QBP1 also inhibits polyglutamine aggregation in transfected COS-7 cells. As was previously demonstrated, COS-7 cells expressing polyglutamine domain fusion proteins are a good cellular model of the polyglutamine repeat diseases because the polyglutamine-fusion proteins mimic the native disease proteins by forming aggregates and by killing cells in a polyglutamine length-dependent pattern (Onodera, O. et al. (1997) *Biochem & Biophys Res Commun* 238, 599–605).

Figure 3A:
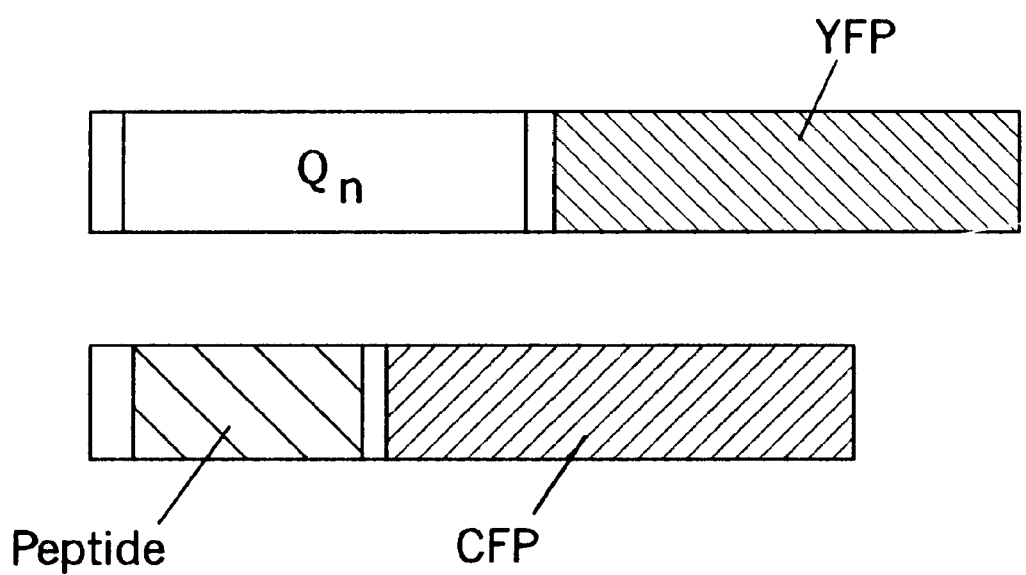
FIG. 3A: Schematic representations of $Q_n$-YFP (upper) and QBP1, RAN or SCR-CFP fusion proteins (lower).

To determine the intracellular distribution of both polyglutamine and QBP1, fusion proteins were designed of polyglutamine with Yellow Fluorescent Protein ($Q_n$-YFP where n=19, 45, 57 or 81 glutamines)) and fused QBP1 with Cyan Fluorescent Protein (QBP1-CFP) (FIG. 3A). YFP and CFP are variants of green fluorescent protein (GFP) with distinct emission spectra, which enable separate detection of each fluorescent protein in double labeled cells (Ellenberg, J. et al. (1999) *Trends Cell Biol* 9, 52–56).

Figure 3B:
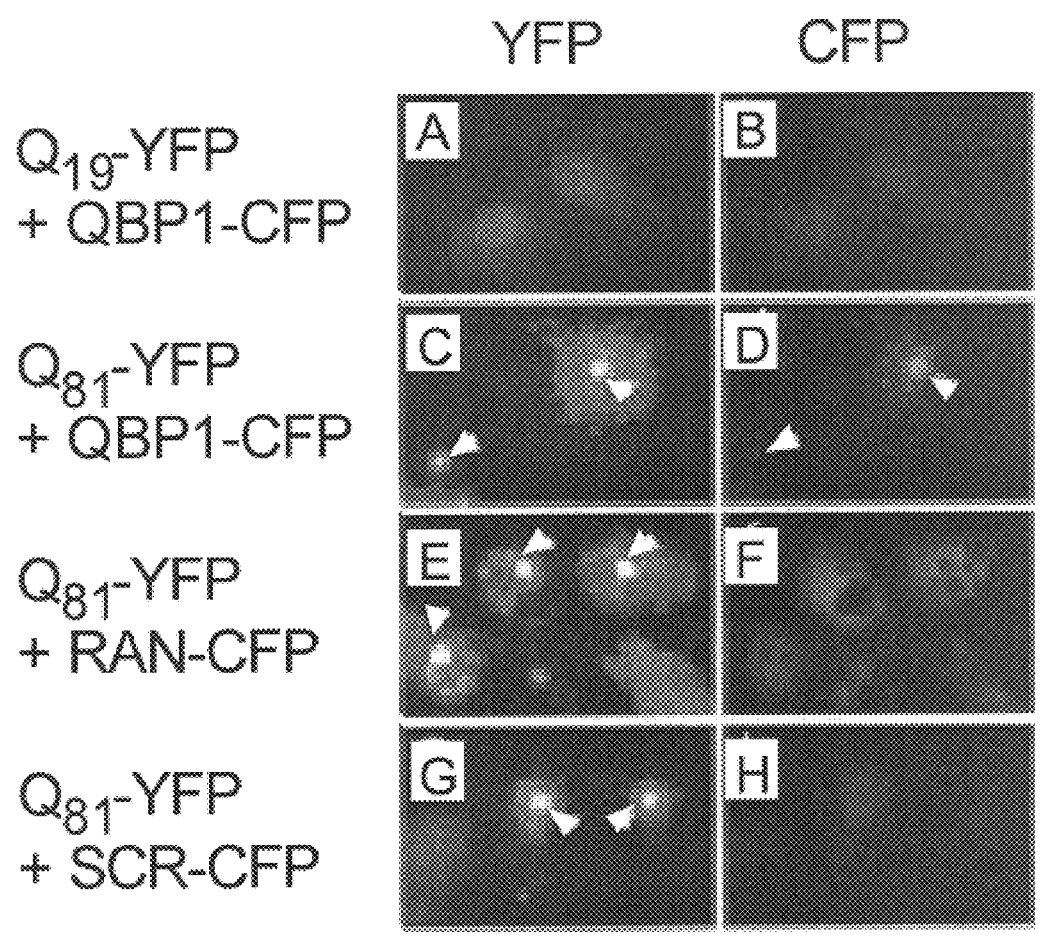
FIG. 3B: Fluorescent micrographs demonstrating co-localization of QBP1-CFP with Q81-YFP aggregates in COS 7 cells 48 hours after transfection. a and b; Co-expression of Q19-YFP and QBP1-CFP, c and d; Q81-YFP and QBP1-CFP, e and f; Q81-YFP and RAN-CFP, g and h; Q81-YFP and SCR-CFP. a, c, e, g; images obtained by YFP filter set (Omega Optical Inc., Brattlesboro, Vt.). b, d, f, h; by CFP filter set (Omega Optical Inc.). No YFP signal could be seen using the CFP filter and no CFP fluorescence was detected using the YFP filter. Magnification×320

QBP1 fused to cyan fluorescent protein (QBP1-CFP) expressed in COS-7 cells remained diffusely distributed (not shown). A polyglutamine-yellow fluorescent fusion protein with 19 glutamines ($Q_{19}$-YFP) was also diffusely distributed and its distribution was unaffected by co-expression with QBP1-CFP (FIG. 3B, a and b). Expression of a pathologic-length polyglutamine-YFP fusion protein with 81 glutamines ($Q_{18}$-YFP) in transfected cells formed aggregate. Co-expression of the polyglutamine-YFP with 81 glutamines ($Q_{81}$-YFP) and QBP1-CFP produced co-localization of these two fluorescent proteins in the protein aggregates (FIG. 3B, c and d). In contrast, random peptide or scrambled peptide fused to CFP (RAN-CFP and SCR-CFP) did not co-localize with the aggregate formed by polyglutamine-YFP containing 81 glutamine ($Q_{81}$-YFP) (FIG. 3B, e-h).

EXAMPLE 11

QBP1 Inhibits Polyglutamine Aggregate Formation in Cells

Figure 4:
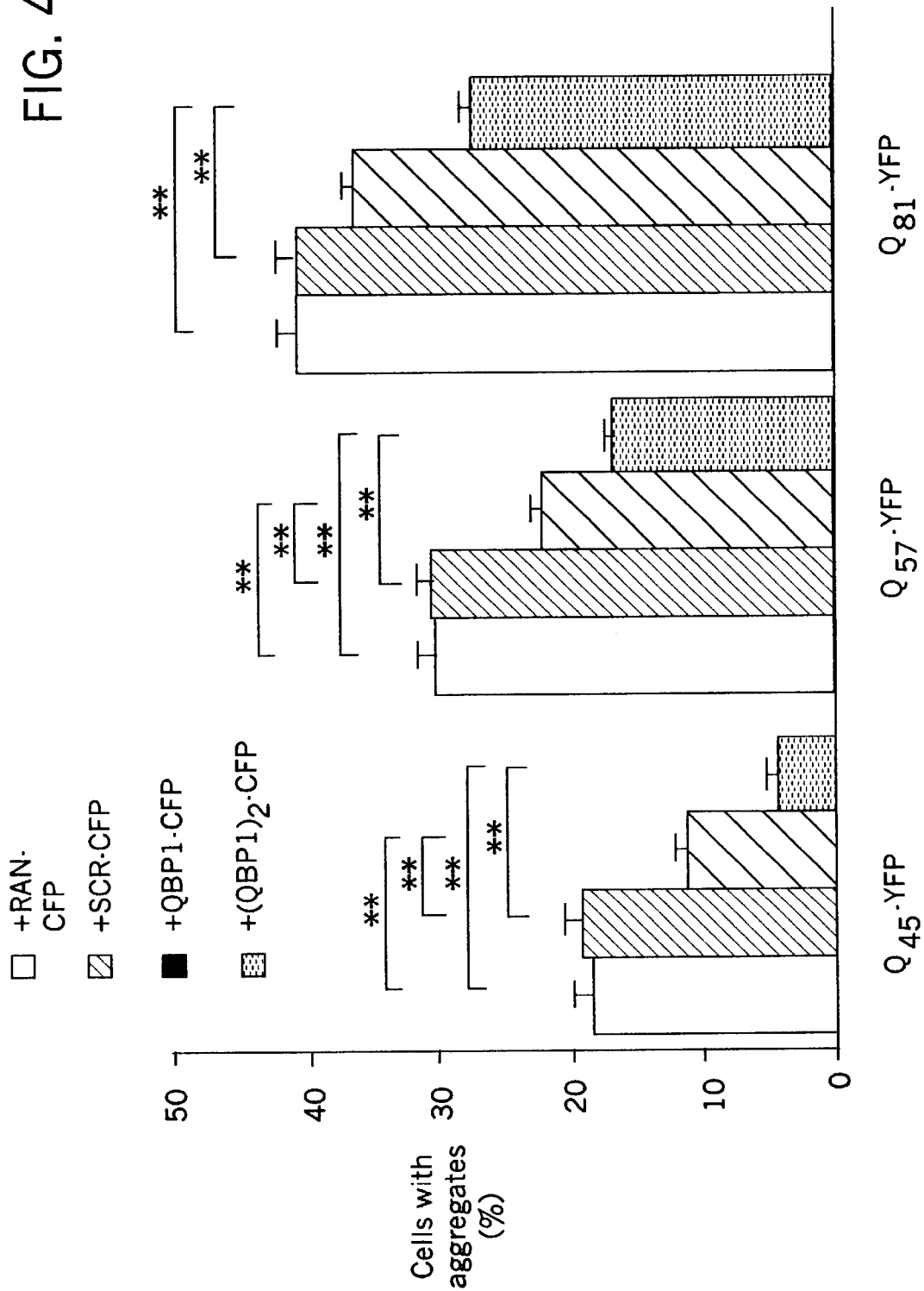
FIG. 4. QBP1 expression decreases the number of cells containing polyglutamine aggregates. Open bar=cells co-transfected with $Q_n$-YFP and RAN-CFP. Hatched bar= cells co-transfected with $Q_n$-YFP and SCR-CFP. Filled bar=cells co-transfected with $Q_n$-YFP and QBP1-CFP. Dotted bar=cells co-transfected with $Q_n$-YFP and (QBP1)$_2$-CFP.

Next, the effect of QBP1-CFP expression on polyglutamine-YFP ($Q_n$-YFP) aggregate formation in co-transfected COS-7 cells was examined. Diffuse fluorescence was easily distinguishable from aggregate using the fluorescence microscope (Compare diffuse fluorescence of polyglutamine in FIG. 3B a with punctate fluorescence of aggregated protein in FIG. 3B c, e and g.). Co-expression of QBP1-CFP reduced the percentage of cells with polyglutamine aggregates (FIG. 4). Inhibition of polyglutamine aggregation by QBP1-CFP was most pronounced with shorter pathologic-length glutamine fusion proteins (45 glutamines ($Q_{45}$)>57 glutamines ($Q_{57}$)>81 glutamines ($Q_{81}$)). Compared to cells co-expressing random peptide-CFP (RAN-CFP), QBP1-CFP reduced aggregation of polyglutamine-YFP with 45 glutamines ($Q_{45}$-YFP) by 39% (FIG. 4; p<0.01). QBP1 also reduced aggregation of polyglutamine-YFP with 57 glutamines ($Q_{57}$-YFP) by 26% (p<0.01). A trend toward decreasing aggregation was seen in cells transfected with QBP1 and polyglutamine-YFP containing 81 glutamines ($Q_{81}$-YFP) but the difference did not reach statistical significance (p=0.073). The decline in QBP1-CFP's ability to inhibit aggregation of proteins with increasingly long polyglutamine domains in cells is consistent with our in vitro data showing QBP1 is less effective at inhibiting aggregation of thioredoxin-polyglutamine with 81 glutamines (thio-$Q_{81}$) compared to thioredoxin-polyglutamine with 62 glutamines (thio-$Q_{62}$). To determine if duplication of the sequence of QBP1 would affect its ability to inhibit polyglutamine aggregation a tandem repeat of QBP1 was prepared and fused to CFP. Tandem-QBP1-CFP (($QBP1)_2$-CFP) is more effective at inhibiting all lengths of polyglutamine-YFP aggregation than monomer QBP1-CFP (FIG. 4; Dotted bars). Scrambled peptide fused to CFP (SCR-CFP) did not alter aggregation of cells expressing polyglutamine-CFP with 45, 57 or 81 glutamines ($Q_{45,57\ or\ 81}$-YFP) (FIG. 4; Hatched bars).

EXAMPLE 12

Polyglutamine Binding Peptide Inhibits Cell Death

The relationship between polyglutamine protein aggregation and cell death is controversial. To determine whether QBP1 or tandem-QBP1 inhibit polyglutamine-induced cell death, cell membrane permeability to ethidium homodimer was assayed. The membranes of living cells are impermeable to ethidium homodimer and permeability to ethidium homodimer is a well-established measure of cell death. Ethidium homodimer undergoes a 30-fold increase in fluorescence upon binding to nucleic acid allowing easy detection with a fluorescence microscope using a rhodamine filter. QBP1 and tandem QBP1 (($QBP1)_2$) fused to CFP inhibit $Q_{57}$-YFP induced cell death (FIG. 5). As with inhibition of aggregation, tandem QBP1 (($QBP1)_2$) is more effective at inhibiting cell death than monomer QBP1. Similar results have also been observed with Q45- and $Q_{81}$-YFP (not shown). Scrambled QBP1 fused to CFP (SCR) does not inhibit cell death (FIG. 5).

EXAMPLE 13

Inhibition of PolyGlutamine-Thioredoxin Aggregation by Additional Peptides

FIG. 6 and FIG. 7 illustrate the inhibition of polyglutamine-thioredoxin aggregation by a variety of different peptides at 1 and 10 microMolar concentrations, in accordance with procedures as described above. From these graphs, it will be noted that the peptide WKWW (SEQ ID NO:1) alone does not exhibit substantial inhibition of aggregation. The peptide WKWWPGIF (QPB1-M8) (SEQ ID NO:12) retains full inhibitory activity. WKWWPFD (QPB1-M7FD) (SEQ ID NO:14) has some activity at high concentration, indicating that the proline contributes to the inhibition of aggregation. Removal of the proline (QPB1-M&FD vs. QBP1-M6FD) results in a significant loss of activity, further indicating the importance of the proline residue.

The following table displays the effect of additional peptides on aggregation of thioredoxin-polyglutamine protein containing 62 glutamines.

| Peptide Sequence* | Ability to Inhibit Aggregation |
|---|---|
| WKWWPGIFD (SEQ ID NO:27) | ++++ |
| WVWWPGIFD (SEQ ID NO:28) | +++ |
| WDWWPGIFD (SEQ ID NO:29) | ++ |
| WWWWPGIFD (SEQ ID NO:30) | ++ |
| WLWWPGIFD (SEQ ID NO:31) | ++ |
| WKWVVWKWWP (SEQ ID NO:32) | ++++ |
| WKWWPWKWW (SEQ ID NO:16) | +++ |
| WKWWVWKWW (SEQ ID NO:33) | ++ |

*5 μm peptide and 15 μM thio-polyglutamine.

Peptides containing membrane transport sequence (TAT) fused to polyglutamine binding peptide.

| Peptide Sequence** | Ability to Inhibit Aggregation |
|---|---|
| WKWWPGIFD-TAT (SEQ ID NO:34) | +++ |
| WKWWPWKWW-TAT (SEQ ID NO:35) | ++++ |
| WKWWVWKWWP-TAT (SEQ ID NO:36) | ++++ |

**10 μm peptide and 15 μM thio-polyglutamine. Scale: Inhibition of aggregation of thioredoxin-polyglutamine containing 62 glutamines for 10 days: ++++ = full inhibition; +++ = 75% inhibition; ++ = 50% inhibition + =25% inhibition.

EXAMPLE 14

Inhibition of Polyglutamine-Thioredoxin Aggregation and Cell Death Using Polyglutamine Binding Peptides Fused to the Membrane Transport Sequence of TAT Protein Several proteins can ferry peptides or proteins into cells through the plasma membrane including HIV transactivator protein (TAT) (SEQ ID NO:37), antennapedia (SEQ ID NO:38), and herpes simplex virus type 1 protein 22 (SEQ ID NO:39) (Prochiantz, *Curr Opin Cell Biol.* 12:400–406 (2000)). These diverse proteins possess similar arginine-rich sequences that mediate transport across cell membranes. The arginine-rich domains of these proteins are sufficient to transport some intact proteins even when fused to non-native proteins. The ability of polyglutamine-binding peptides fused to a TAT fragment to enter transfected COS 7 cells and inhibit polyglutamine aggregation and cell death was examined. Transfected COS 7 cells expressing $Q_{81}$-YFP developed aggregates in 32.7% (+/–4.0% SEM) of cells when treated with a random peptide fused to TAT and 9.8% of transfected cells died within 72 hours. Addition of the peptide WKWWPGIFD (SEQ ID NO:27) to transfected COS 7 cells had no effect on aggregation or cell death. In contrast, addition of TAT-WKWWPGIFD (SEQ ID NO:34) to transfected cells inhibited $Q_{81}$-YFP aggregation by 32% (22.1% +/–3.5% SEM aggregation; $p<6.6\times10^{-4}$) and cell death by 39% (6.0% +/–1.7% SEM cell death; $p<1.52\times10^{-3}$).

A polyarginine sequence as a membrane transport peptide was also examined and shown to inhibit in vitro polyglutamine aggregation as well as aggregation and death in cells. The arginine containing peptide sequence that inhibits aggregation in vitro and in cells and cell death is: WKWWPGIFD-GGRRRRRRRR (SEQ ID NO:40).

The foregoing is illustrative of the present invention, and is not to be construed as limiting thereof. The invention is defined by the following claims, with equivalents of the claims to be included therein.

That which is claimed is:

1. A method of detecting an expanded polyglutamine domain in a sample suspected of containing an expanded polyglutamine domain, said expanded polyglutamine domain consisting of at least 40 glutamine residues, said method comprising the steps of:

(a) contacting a sample with a compound according to Formula I:

$$X_1—R^{11}R^{12}R^{13}R^{14}—Y^1 \quad (I)$$

wherein:

$R^{11}$ is Trp;

$R^{12}$ is (i) Trp or (ii) a charged amino acid selected from the group consisting of Lys, Arg and His;

$R^{13}$ is (i) Trp or (ii) a charged amino acid selected from the group consisting of Lys, Arg and His;

subject to the proviso that one of $R^{12}$ and $R^{13}$ is Trp and the other is a charged amino acid;

$R^{14}$ is Trp;

$X^1$ is a peptide consisting of from 1 to 10 standard amino acids, or is deleted and $Y^1$ is a peptide consisting of from 1 to 10 standard amino acids, or is deleted or a physiologically acceptable salt thereof, which compound binds to an expanded polyglutamine domain; and then (b) determining Whether the compound binds with the sample, the presence of binding indicating the presence of an expanded polyglutamine domain in said sample.

2. A method according to claim 1, wherein said compound is conjugated to a detectable group, and wherein said determining step is carried out by determining the presence or absence of binding of said detectable group to said sample.

3. A method according to claim 1, wherein said compound is conjugated to thioredoxin, and said detecting step is carried out by turbidometric assay.

4. A method according to claim 1, wherein said sample comprises a protein.

5. A method according to claim 1, wherein said sample comprises a protein collected from a patient.

6. A method according to claim 1, wherein said protein is selected from the group consisting of huntingtin, atrophin 1, ataxin 1, ataxin 2, ataxin 6, ataxin 7, and androgen receptor protein.

* * * * *

UNITED STATES PATENT AND TRADEMARK OFFICE
CERTIFICATE OF CORRECTION

PATENT NO.   : 6,632,616 B2
DATED        : October 14, 2003
INVENTOR(S)  : Burke et al.

It is certified that error appears in the above-identified patent and that said Letters Patent is hereby corrected as shown below:

Column 37,
Line 34, should read -- $X^1\text{-}R^{11}R^{12}R^{13}R^{14}\text{-}Y^1$    (I) --

Signed and Sealed this

Twentieth Day of April, 2004

JON W. DUDAS
*Acting Director of the United States Patent and Trademark Office*

SEQUENCE LISTING

```
<160> NUMBER OF SEQ ID NOS: 40

<210> SEQ ID NO 1
<211> LENGTH: 4
<212> TYPE: PRT
<213> ORGANISM: synthetic construct

<400> SEQUENCE: 1

Trp Lys Trp Trp
1

<210> SEQ ID NO 2
<211> LENGTH: 4
<212> TYPE: PRT
<213> ORGANISM: synthetic construct

<400> SEQUENCE: 2

Trp Trp Lys Trp
1

<210> SEQ ID NO 3
<211> LENGTH: 11
<212> TYPE: PRT
<213> ORGANISM: synthetic construct

<400> SEQUENCE: 3

Ser Asn Trp Lys Trp Trp Pro Gly Ile Phe Asp
1               5                   10

<210> SEQ ID NO 4
<211> LENGTH: 22
<212> TYPE: PRT
<213> ORGANISM: synthetic construct
```

```
<400> SEQUENCE: 4

Ser Asn Trp Lys Trp Trp Pro Gly Ile Phe Asp Ser Asn Trp Lys Trp
1               5                   10                  15
Trp Pro Gly Ile Phe Asp
            20

<210> SEQ ID NO 5
<211> LENGTH: 8
<212> TYPE: PRT
<213> ORGANISM: synthetic construct

<400> SEQUENCE: 5

Trp Lys Trp Trp Trp Lys Trp Trp
1               5

<210> SEQ ID NO 6
<211> LENGTH: 5
<212> TYPE: PRT
<213> ORGANISM: synthetic construct

<400> SEQUENCE: 6

Trp Lys Trp Trp Pro
1               5

<210> SEQ ID NO 7
<211> LENGTH: 5
<212> TYPE: PRT
<213> ORGANISM: synthetic construct

<400> SEQUENCE: 7

Pro Trp Trp Lys Trp
1               5

<210> SEQ ID NO 8
<211> LENGTH: 6
<212> TYPE: PRT
<213> ORGANISM: synthetic construct

<400> SEQUENCE: 8

Trp Lys Trp Trp Pro Gly
1               5

<210> SEQ ID NO 9
<211> LENGTH: 6
<212> TYPE: PRT
<213> ORGANISM: synthetic construct

<400> SEQUENCE: 9

Gly Pro Trp Trp Lys Trp
1               5

<210> SEQ ID NO 10
<211> LENGTH: 7
<212> TYPE: PRT
<213> ORGANISM: synthetic construct

<400> SEQUENCE: 10

Trp Lys Trp Trp Pro Gly Ile
1               5

<210> SEQ ID NO 11
<211> LENGTH: 7
<212> TYPE: PRT
<213> ORGANISM: synthetic construct
```

```
<400> SEQUENCE: 11

Ile Gly Pro Trp Trp Lys Trp
1               5

<210> SEQ ID NO 12
<211> LENGTH: 8
<212> TYPE: PRT
<213> ORGANISM: synthetic construct

<400> SEQUENCE: 12

Trp Lys Trp Trp Pro Gly Ile Phe
1               5

<210> SEQ ID NO 13
<211> LENGTH: 8
<212> TYPE: PRT
<213> ORGANISM: synthetic construct

<400> SEQUENCE: 13

Phe Ile Gly Pro Trp Trp Lys Trp
1               5

<210> SEQ ID NO 14
<211> LENGTH: 7
<212> TYPE: PRT
<213> ORGANISM: synthetic construct

<400> SEQUENCE: 14

Trp Lys Trp Trp Pro Phe Asp
1               5

<210> SEQ ID NO 15
<211> LENGTH: 7
<212> TYPE: PRT
<213> ORGANISM: synthetic construct

<400> SEQUENCE: 15

Asp Phe Pro Trp Trp Lys Trp
1               5

<210> SEQ ID NO 16
<211> LENGTH: 9
<212> TYPE: PRT
<213> ORGANISM: synthetic construct

<400> SEQUENCE: 16

Trp Lys Trp Trp Pro Trp Lys Trp Trp
1               5

<210> SEQ ID NO 17
<211> LENGTH: 9
<212> TYPE: PRT
<213> ORGANISM: synthetic construct

<400> SEQUENCE: 17

Trp Trp Lys Trp Pro Trp Trp Lys Trp
1               5

<210> SEQ ID NO 18
<211> LENGTH: 6
<212> TYPE: PRT
<213> ORGANISM: synthetic construct

<400> SEQUENCE: 18
```

Trp Lys Trp Trp Phe Asp
1               5

<210> SEQ ID NO 19
<211> LENGTH: 6
<212> TYPE: PRT
<213> ORGANISM: synthetic construct

<400> SEQUENCE: 19

Phe Asp Trp Trp Lys Trp
1               5

<210> SEQ ID NO 20
<211> LENGTH: 11
<212> TYPE: PRT
<213> ORGANISM: synthetic construct

<400> SEQUENCE: 20

His Trp Trp Arg Ser Trp Tyr Ser Asp Ser Val
1               5                   10

<210> SEQ ID NO 21
<211> LENGTH: 11
<212> TYPE: PRT
<213> ORGANISM: synthetic construct

<400> SEQUENCE: 21

His Glu Trp His Trp Trp His Gln Glu Ala Ala
1               5                   10

<210> SEQ ID NO 22
<211> LENGTH: 11
<212> TYPE: PRT
<213> ORGANISM: synthetic construct

<400> SEQUENCE: 22

Trp Gly Leu Glu His Phe Ala Gly Asn Lys Arg
1               5                   10

<210> SEQ ID NO 23
<211> LENGTH: 11
<212> TYPE: PRT
<213> ORGANISM: synthetic construct

<400> SEQUENCE: 23

Trp Trp Arg Trp Asn Trp Ala Thr Pro Val Asp
1               5                   10

<210> SEQ ID NO 24
<211> LENGTH: 11
<212> TYPE: PRT
<213> ORGANISM: synthetic construct

<400> SEQUENCE: 24

Trp His Asn Tyr Phe His Trp Trp Gln Asp Thr
1               5                   10

<210> SEQ ID NO 25
<211> LENGTH: 11
<212> TYPE: PRT
<213> ORGANISM: synthetic construct

<400> SEQUENCE: 25

Trp Pro Ile Trp Ser Lys Gly Asn Asp Trp Phe

-continued

```
1               5               10

<210> SEQ ID NO 26
<211> LENGTH: 11
<212> TYPE: PRT
<213> ORGANISM: synthetic construct

<400> SEQUENCE: 26

Leu Ser Leu Met Glu Phe Gly Cys Arg Gly Ala
1               5               10

<210> SEQ ID NO 27
<211> LENGTH: 9
<212> TYPE: PRT
<213> ORGANISM: synthetic construct

<400> SEQUENCE: 27

Trp Lys Trp Trp Pro Gly Ile Phe Asp
1               5

<210> SEQ ID NO 28
<211> LENGTH: 9
<212> TYPE: PRT
<213> ORGANISM: synthetic construct

<400> SEQUENCE: 28

Trp Val Trp Trp Pro Gly Ile Phe Asp
1               5

<210> SEQ ID NO 29
<211> LENGTH: 9
<212> TYPE: PRT
<213> ORGANISM: synthetic construct

<400> SEQUENCE: 29

Trp Asp Trp Trp Pro Gly Ile Phe Asp
1               5

<210> SEQ ID NO 30
<211> LENGTH: 9
<212> TYPE: PRT
<213> ORGANISM: synthetic construct

<400> SEQUENCE: 30

Trp Trp Trp Trp Pro Gly Ile Phe Asp
1               5

<210> SEQ ID NO 31
<211> LENGTH: 9
<212> TYPE: PRT
<213> ORGANISM: synthetic construct

<400> SEQUENCE: 31

Trp Leu Trp Trp Pro Gly Ile Phe Asp
1               5

<210> SEQ ID NO 32
<211> LENGTH: 10
<212> TYPE: PRT
<213> ORGANISM: synthetic construct

<400> SEQUENCE: 32

Trp Lys Trp Trp Val Trp Lys Trp Trp Pro
1               5               10
```

<210> SEQ ID NO 33
<211> LENGTH: 9
<212> TYPE: PRT
<213> ORGANISM: synthetic construct

<400> SEQUENCE: 33

Trp Lys Trp Trp Val Trp Lys Trp Trp
1               5

<210> SEQ ID NO 34
<211> LENGTH: 22
<212> TYPE: PRT
<213> ORGANISM: synthetic construct

<400> SEQUENCE: 34

Trp Lys Trp Trp Pro Gly Ile Phe Asp Gly Gly Tyr Gly Arg Lys Lys
1               5                   10                  15

Arg Arg Gln Arg Arg
            20

<210> SEQ ID NO 35
<211> LENGTH: 22
<212> TYPE: PRT
<213> ORGANISM: synthetic construct

<400> SEQUENCE: 35

Trp Lys Trp Trp Pro Trp Lys Trp Trp Gly Gly Tyr Gly Arg Lys Lys
1               5                   10                  15

Arg Arg Gln Arg Arg
            20

<210> SEQ ID NO 36
<211> LENGTH: 23
<212> TYPE: PRT
<213> ORGANISM: synthetic construct

<400> SEQUENCE: 36

Trp Lys Trp Trp Val Trp Lys Trp Trp Pro Gly Gly Tyr Gly Arg Lys
1               5                   10                  15

Lys Arg Arg Gln Arg Arg Arg
            20

<210> SEQ ID NO 37
<211> LENGTH: 11
<212> TYPE: PRT
<213> ORGANISM: Human immunodeficiency virus

<400> SEQUENCE: 37

Tyr Gly Arg Lys Lys Arg Arg Gln Arg Arg
1               5                   10

<210> SEQ ID NO 38
<211> LENGTH: 16
<212> TYPE: PRT
<213> ORGANISM: Drosophila melanogaster

<400> SEQUENCE: 38

Arg Gln Ile Lys Ile Trp Phe Gln Asn Arg Arg Met Lys Trp Lys Lys
1               5                   10                  15

<210> SEQ ID NO 39
<211> LENGTH: 34
<212> TYPE: PRT

```
<213> ORGANISM: herpes simplex virus type 1

<400> SEQUENCE: 39

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 40
<211> LENGTH: 19
<212> TYPE: PRT
<213> ORGANISM: synthetic construct

<400> SEQUENCE: 40

Trp Lys Trp Trp Pro Gly Ile Phe Asp Gly Gly Arg Arg Arg Arg Arg
1               5                   10                  15

Arg Arg Arg
```